(12) United States Patent
Sansoucy

(10) Patent No.: US 7,211,074 B2
(45) Date of Patent: May 1, 2007

(54) VALVED CATHETER

(75) Inventor: Michael Sansoucy, Plainville, MA (US)

(73) Assignee: Sherwood Services AG, Schaffhausen (CH)

( * ) Notice: Subject to any disclaimer, the term of this patent is extended or adjusted under 35 U.S.C. 154(b) by 196 days.

(21) Appl. No.: 10/639,792

(22) Filed: Aug. 12, 2003

(65) Prior Publication Data

US 2005/0038413 A1    Feb. 17, 2005

(51) Int. Cl.
A61M 25/16    (2006.01)
(52) U.S. Cl. .................. 604/537; 604/43; 604/249; 604/33
(58) Field of Classification Search ............ 604/96.01, 604/264, 523, 99.02–99.04, 27–31, 33, 39–44, 604/36, 167.01–167.06, 401, 5.01–5.04, 604/6.01–6.16, 249, 236, 537, 533, 238, 604/245, 246–247, 93.01
See application file for complete search history.

(56) References Cited

U.S. PATENT DOCUMENTS

| | | | |
|---|---|---|---|
| 701,075 A | 5/1902 | McCully | |
| 4,134,402 A * | 1/1979 | Mahurkar | 604/44 |
| 4,583,968 A | 4/1986 | Mahurkar | 604/43 |
| 4,675,004 A | 6/1987 | Hadford et al. | 604/44 |
| 4,682,978 A | 7/1987 | Martin | 604/43 |
| 4,808,155 A | 2/1989 | Mahurkar | 604/43 |
| 4,842,582 A | 6/1989 | Mahurkar | 604/43 |
| 5,009,636 A | 4/1991 | Wortley et al. | 604/43 |
| 5,209,723 A | 5/1993 | Twardowski et al. | 604/43 |
| 5,267,979 A | 12/1993 | Appling et al. | 604/247 |
| 5,374,245 A | 12/1994 | Mahurkar | 604/43 |
| 5,399,172 A | 3/1995 | Martin et al. | 604/248 |
| 5,403,291 A | 4/1995 | Abrahamson | 604/280 |
| 5,464,398 A | 11/1995 | Haindl | 604/280 |
| 5,569,182 A | 10/1996 | Twardowski et al. | 604/43 |
| 5,685,867 A | 11/1997 | Twardowski et al. | 604/280 |
| 5,858,009 A | 1/1999 | Jonkman | 604/264 |

(Continued)

FOREIGN PATENT DOCUMENTS

WO    WO 92/14500    9/1992

(Continued)

Primary Examiner—Nicholas Lucchesi
Assistant Examiner—Theodore J. Stigell
(74) Attorney, Agent, or Firm—Carter, Deluca, Farrell, Schmidt, LLP

(57) ABSTRACT

A catheter apparatus is provided that includes a tubular body having a distal end. The body defines first and second lumens. The first lumen has a first adapter that includes a first valve biased to seal the proximal end. The first lumen defines a first lateral port and the second lumen defines a second lateral port. A push rod is connected to the first valve for corresponding movement therewith and extends to a tip. The tip includes a first member extending into the first lumen and a second member extending into the second lumen such that the first member seals the first lateral port and the second member seals the second lateral port in a closed position of the tip. The first valve is engageable such that fluid communication is established between the proximal end of the first lumen and the first lumen, and the first and second members move to an open position whereby fluid communication is established. The first and second lumens may be coaxial whereby the first lumen has a first port that seals a second port of the second lumen.

14 Claims, 18 Drawing Sheets

U.S. PATENT DOCUMENTS

| | | |
|---|---|---|
| 5,961,486 A | 10/1999 | Twardowski et al. ......... 604/43 |
| 6,190,371 B1 * | 2/2001 | Maginot et al. ............ 604/523 |
| 6,409,700 B1 | 6/2002 | Siegel, Jr. et al. ............ 604/43 |
| 2002/0065492 A1 | 5/2002 | McGuckin, Jr. et al. |
| 2005/0177094 A1 * | 8/2005 | Igarashi et al. ............... 604/43 |

FOREIGN PATENT DOCUMENTS

| | | |
|---|---|---|
| WO | WO 97/44085 | 11/1997 |
| WO | WO 99/38550 | 8/1999 |
| WO | WO 01/10485 A1 | 2/2001 |

* cited by examiner

VALVED CATHETER

BACKGROUND

1. Technical Field

The present disclosure generally relates to medical catheter apparatus and, more particularly, to a multiple lumen catheter apparatus that facilitates bi-directional fluid flow.

2. Description of the Related Art

Some known catheters are tubular, flexible medical devices for administration of fluids (withdrawal, introduction, etc.) with cavities, ducts, vessels, etc. of a body. Typically, catheter devices are inserted with the cavity of a body via a sheath, stylet, trocar, etc.

These catheter devices may be employed for administration of fluids that includes the simultaneous introduction and withdrawal of fluid for applications such as, surgery, treatment, diagnosis, etc. For example, in one particular hemodialysis application, blood is withdrawn from a blood vessel for treatment by an artificial kidney device and the treated blood is introduced back into the blood vessel. Various known catheter devices have been employed for simultaneous withdrawal and introduction of fluid with a body. Some devices use two separate needles or catheters. These devices, however, require two separate punctures with the associated discomfort, possibility for infection, and consequent trauma to the blood vessels. Other devices employ dual lumen catheters to facilitate bi-directional fluid flow whereby one lumen performs withdrawal of blood and the other lumen introduces treated blood to the vessel.

The above mentioned catheter devices, however, typically require clamping of the tubular portions or lumens when fluid administration is not being performed. This type of structure can result in several drawbacks. For example, blood can remain in the lumen causing thrombosis in the line and/or at the tip of the device. This results in a flow restriction that can significantly reduce flow rate. Further, the clamps of these catheter devices may fail and/or may cause damage or deformation to the extension lines, particularly in those devices employed for extended periods of use, such as chronic catheters. Failure may result in undesirable blood evacuation, heparin leakage, etc. Moreover, devices employing clamps are generally bulky and cumbersome.

Therefore, it would be desirable to overcome the disadvantages and drawbacks of the prior art with a catheter apparatus that facilitates bi-directional fluid flow by employing a multiple lumen body having a valve configuration that prevents thrombosis. It would be desirable if such a catheter apparatus included a multiple valve configuration that prevents undesirable blood evacuation and anti-coagulant leakage. It would be highly desirable if the catheter apparatus had a smaller relative design to achieve the principles of the present disclosure. It is contemplated that the catheter apparatus and its constituent parts are easily and efficiently manufactured and assembled.

SUMMARY

Accordingly, a catheter apparatus is provided that facilitates bi-directional fluid flow by employing a multiple lumen body having a valve configuration that prevents thrombosis and may break up fibrin sheath to overcome the disadvantages and drawbacks of the prior art. Desirably, such a catheter apparatus includes a multiple valve configuration that prevents blood evacuation and anti-coagulant leakage. Most desirably the catheter apparatus has a smaller relative design to achieve the principles of the present disclosure. The catheter apparatus is easily and efficiently manufactured and assembled. The present disclosure resolves related disadvantages and drawbacks experienced in the art.

In one particular embodiment, a dialysis catheter is provided with a tip that moves in and out of the catheter, to expose an arterial lumen and a venous lumen, for use and sealing when not in use. The motion of the tip results from attaching a blood line to the device whereby a male luer fitting pushes on a push rod of the device, as will be discussed.

Some of the advantages of the catheter device of the present disclosure include the arterial and/or venous lumens being sealed from blood contact when not in use. This configuration minimizes thrombosis and heparin leakage. Further, when the catheter device is not being employed, clamps are not required to prevent leakage. Thus, blood evacuation risk is minimized.

In another embodiment, the catheter device of the present disclosure includes a dual lumen catheter used for transdermal catheter related procedures, including hemodialysis. Upon attachment of appropriate blood lines, the device includes a normally closed arterial lumen that can be opened at the tip of the device to allow blood flow into the device. A normally closed valve within the hub of the device, including a luer fitting, can be opened to allow blood flow. The venous lumen may be similarly actuated. It is contemplated that the venous lumen is normally open at the tip of the device.

Other advantages of the catheter device include a reduced size that results in increased subject comfort. The tip of the catheter device allows for aspiration through an angle of 360 degrees. This facilitates a plurality of orientations and prevents positional occlusion. The tip of the device is axially movable relative to the lumens thereby disrupting fibrin sheath formation.

In one particular embodiment, the catheter apparatus includes a tubular body having a distal end. The body defines a first lumen and a second lumen. The first lumen includes a first adapter extending to a proximal end thereof. The first adapter includes a first valve biased to seal the proximal end. The first lumen defines a first lateral port and the second lumen defines a second lateral port adjacent the distal end of the body. A push rod is connected to the first valve for corresponding movement therewith and extends to a tip disposed adjacent the distal end of the body. The tip includes a first member extending into the first lumen and a second member extending into the second lumen such that the first member seals the first lateral port and the second member seals the second lateral port in a closed position of the tip. The first valve is engageable such that fluid communication is established between the proximal end of the first lumen and the first lumen, and the push rod causes the first and second members to move to an open position of the tip whereby fluid communication is established between the first lateral port and the first lumen, and the second lateral port and the second lumen.

The first lumen and the second lumen may be disposed in a substantially parallel orientation along at least a portion of the body. The first lumen may be configured for fluid flow in a first direction and the second lumen may be configured for fluid flow in a second opposite direction. The first lumen may be configured for venous blood flow and the second lumen may be configured for arterial blood flow. Each of the first lumen and the second lumen can have a substantially D-shaped configuration. The push rod is slidably mounted within the body and disposed between the first lumen and the second lumen. A portion of the push rod may be coaxially mounted with the first adapter.

The tip can include a pointed distal head. The tip may include a reverse umbrella valve that includes the first and second members such that the first and second members are slidable within the first and second lumens, respectively. Movement of the tip can cause the first member to move out of alignment with the first lateral port and the second member to move out of alignment with the second lateral port.

A luer fitting may be mounted with the proximal end of the first lumen. The luer fitting has a pusher that is connected with the first valve. A luer fitting may be mounted with the proximal end of the second lumen. The luer fitting has a pusher that is connected with the second valve. The proximal end of the first lumen may be configured for attachment to a fluid line for introduction of fluid into the first lumen and the first lateral port may be configured for expulsion of the fluid. The second lateral port may be configured for introduction of fluid into the second lumen and a proximal end of the second lumen may be configured for expulsion of the fluid to a receiving fluid line.

In an alternate embodiment, the first adapter defines a valve housing that supports the first valve and a spring that biases the first valve to seal the proximal end. The second lumen may include a second adapter extending to a proximal end thereof. The second adapter may include a second valve biased to seal the proximal end of the second lumen. The second adapter may define a valve housing that supports the second valve and a spring that biases the second valve to seal the proximal end.

The body desirably includes a valve configuration for simultaneously establishing fluid communication between the proximal end of the first lumen and the first lumen, and between the first lateral port and the first lumen, and between the second lateral port and the second lumen.

In another alternate embodiment, the catheter apparatus includes a tubular body having a distal end. The body defines a first lumen and a second lumen in a substantially coaxial orientation along at least a portion of the body. The first lumen includes a first adapter extending to a proximal end thereof. The first adapter has a first valve biased to seal the proximal end. The first lumen defines a first port and the second lumen defines a second port adjacent the distal end of the body. The first lumen has a portion that is connected to the first valve for corresponding movement therewith and the first lumen extends to the first port such that the first port seals the second port in a closed position thereof. The first valve is engageable such that fluid communication is established between the proximal end of the first lumen and the first lumen, such engagement further causing the first port to move to an open position whereby fluid communication is established between the second port and the second lumen.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, as set forth below.

DETAILED DESCRIPTION OF EXEMPLARY EMBODIMENTS

The exemplary embodiments of the catheter apparatus and methods of use disclosed are discussed in terms of medical catheters for the administration of fluids (withdrawal, introduction, etc.) with the body of a subject and more particularly, in terms of a catheter apparatus that facilitates bidirectional fluid flow by employing a multiple lumen body having a valve configuration that prevents thrombosis and fibrin sheath formation. It is envisioned that the present disclosure may be employed with a range of catheter applications including surgical, diagnostic and related treatments of diseases, body ailments, etc. of a subject. It is further envisioned that the principles relating to the catheter apparatus disclosed include employment with various catheter related procedures, such as, for example, hemodialysis, cardiac, abdominal, urinary, intestinal, etc., in chronic, acute, etc. applications. It is contemplated that the catheter apparatus can be used for administration of fluids such as, for example, medication, saline, bodily fluids such as, blood, urine, etc.

In the discussion that follows, the term "proximal" will refer to the portion of a structure that is closer to a practitioner, while the term "distal" will refer to the portion that is further from the practitioner. As used herein, the term "subject" refers to a human patient or other animal. According to the present disclosure, the term "practitioner" refers to a doctor, nurse or other care provider and may include support personnel.

Figure 1:
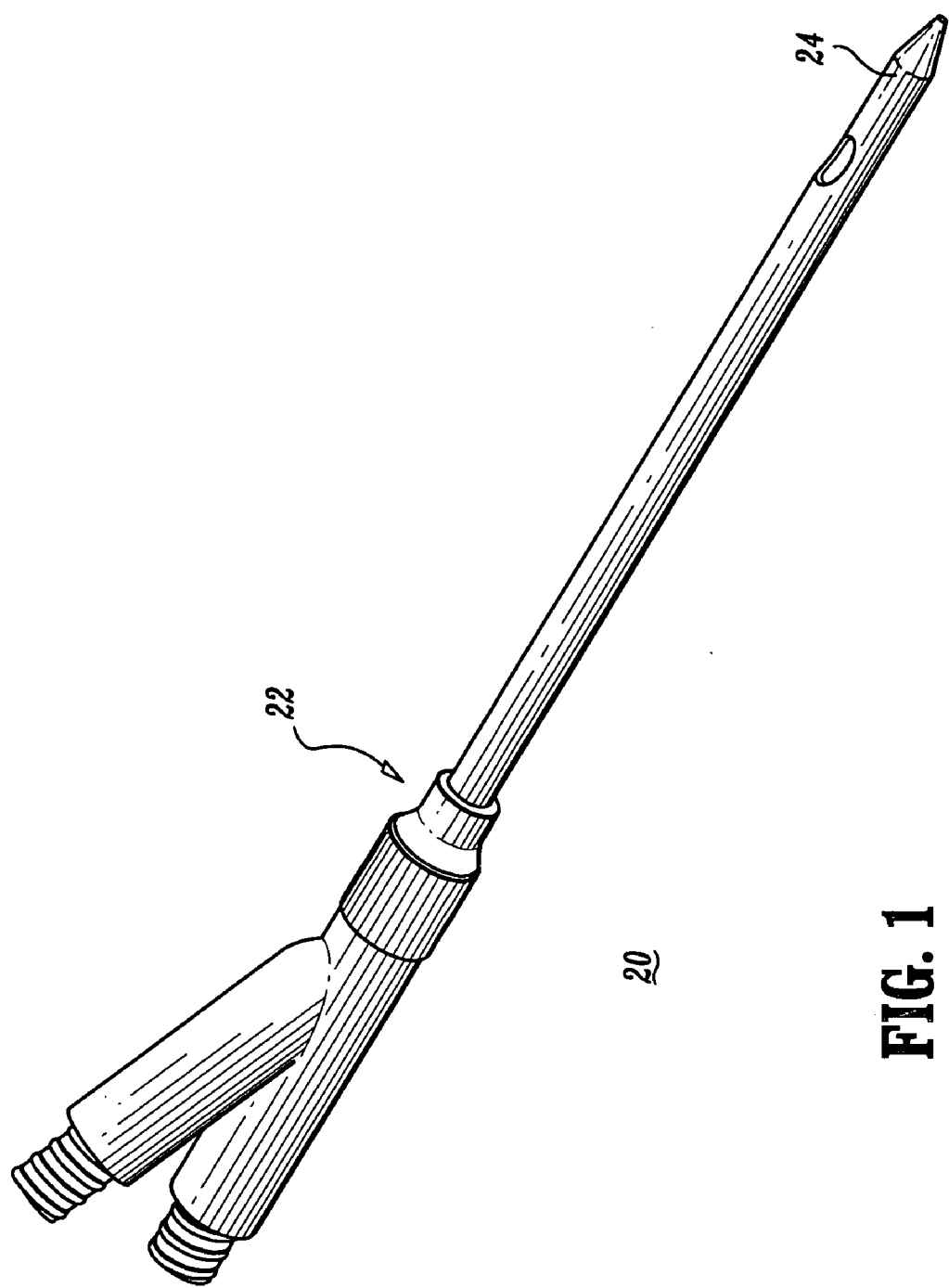
FIG. 1 is a perspective view of a catheter apparatus, in accordance with the principles of the present disclosure.
Figure 2:
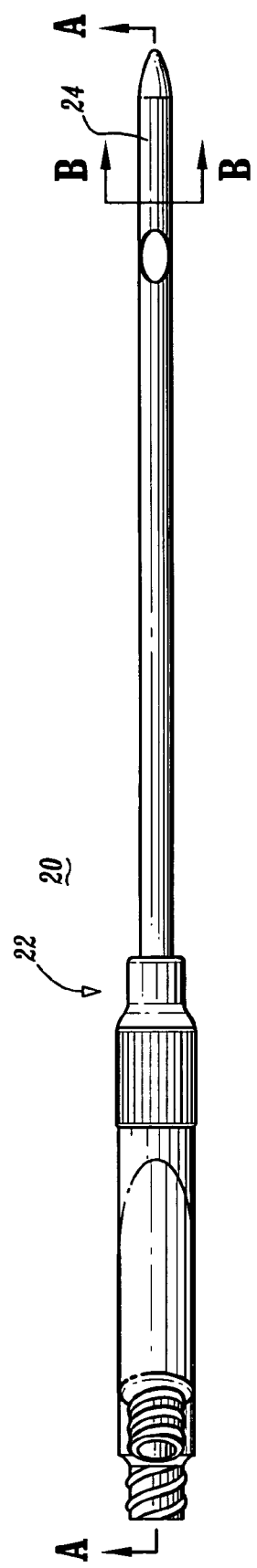
FIG. 2 is a top view of the catheter apparatus shown in FIG. 1.

The following discussion includes a description of the catheter apparatus, followed by a description of an exemplary method of operating the catheter apparatus in accordance with the principles of the present disclosure. Reference will now be made in detail to the exemplary embodiments of the present disclosure, which are illustrated in the accompanying figures. Turning now to the figures wherein like components are designated by like reference numerals throughout the several views and initially to FIGS. 1 and 2, there is illustrated a catheter apparatus 20, in accordance with the principles of the present disclosure.

The components of catheter apparatus 20 are fabricated from materials suitable for medical applications, such as, for example, polymerics or metals, such as stainless steel, depending on the particular catheter application and/or preference of a practitioner. Semi-rigid and rigid polymerics are contemplated for fabrication, as well as resilient materials, such as molded medical grade polypropylene. One skilled in the art, however, will realize that other materials and fabrication methods suitable for assembly and manufacture, in accordance with the present disclosure, also would be appropriate.

Catheter apparatus 20 includes a tubular body 22 having a distal end 24. Tubular body 22 is elongated and has a cylindrical outer surface. It is contemplated that tubular body 22 may be variously dimensioned and attachable to other medical devices. It is further contemplated that the outer surface of tubular body 22 may have various configurations, such as, for example, rectangular, elliptical, polygonal, etc.

Figure 3A:
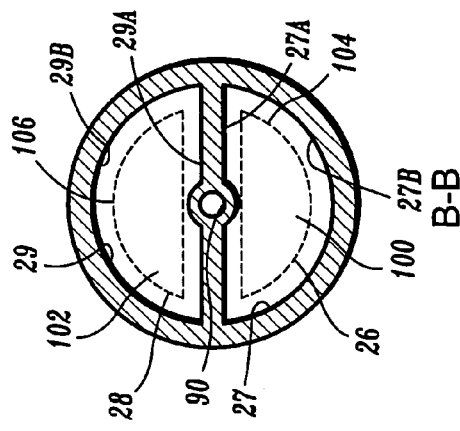
FIG. 3A is a cross-sectional view of the catheter apparatus taken along line B—B of FIG. 2.

Referring to FIGS. 3–8, tubular body 22 defines a first lumen such as, for example, venous lumen 26 and a second lumen such as, for example, arterial lumen 28. Venous lumen 26 and arterial lumen 28 each have a substantially D-shaped or semi-circular configuration. Venous lumen 26 includes an inner surface 27 having a substantially planar portion 27A and a substantially arcuate portion 27B, as shown in FIG. 3A. Arterial lumen 28 includes an inner surface 29 having a substantially planar portion 29A and a substantially arcuate portion 29B. Lumens 26, 28 are elongated with tubular body 22 and inner surfaces 27, 29 are configured to facilitate fluid flow within lumens 26, 28. It is envisioned that lumens 26, 28 may have various configurations, such as, for example, cylindrical, rectangular, elliptical, polygonal, etc.

Venous lumen 26 is configured for fluid flow, such as, for example, venous blood flow, in a first direction, as shown by arrows A. Arterial lumen 28 is configured for fluid flow, such as, for example, arterial blood flow in a second opposite direction, as shown by arrows B. The first and second lumens may be configured for various forms of fluid flow in various directions and orientations, according to the requirements of a particular catheter application.

Lumens 26, 28 may be uniformly dimensioned or include alternative dimensional cross sections within tubular body 22, such as, narrow and broad portions, converging surfaces, undulating surfaces, etc. according to the particular flow indications and/or flow rate requirements. It is contemplated venous lumen 26 and arterial lumen 28 may extend alternative lengths. It is further contemplated that tubular body 22 may include one or a plurality of lumens. It is envisioned that the first lumen may include the arterial lumen and the second lumen may include the venous lumen.

Venous lumen 26 and arterial lumen 28 are disposed in a substantially parallel orientation adjacent a distal portion 30 of tubular body 22. Distal portion 30 may extend various lengths and may include portions of tubular body 22 that are in a non-parallel orientation. It is also contemplated that venous lumen 26 and arterial lumen 28 may be spaced apart.

Venous lumen 26 includes a first adapter, such as, for example, tubular venous adapter 32 that extends to a proximal end 34 thereof. Venous adapter 32 defines a valve housing 36 adjacent proximal end 34. Valve housing 36 has a cylindrical configuration to facilitate support of a first valve 38 and a spring 40 that biases first valve 38, in a substantially proximal direction as shown by arrow C, to seal proximal end 34. Spring 40 may be fixedly mounted to an inner surface of valve housing 36. A first luer fitting 42 is mounted with proximal end 34. First luer fitting 42 includes a first pusher 44 that is connected with first valve 38. It is contemplated that first pusher 44 may be separately formed from first valve 38 and disposed for engagement therewith.

Spring 40 expands, via a spring force thereof, to engage first valve 38, forcing first valve 38 in the direction shown by arrow C. As first valve 38 moves, a surface 46 of first valve 38 engages a surface 48 of proximal end 34. This engagement creates a fluid tight seal between first valve 38 and proximal end 34. The seal prevents inflow of fluids into venous lumen 26 and prevents leakage of fluids therefrom. First valve 38, being connected to first pusher 44, causes first pusher 44 to move in the direction shown by arrow C, and protrude from proximal end 34 for engagement with a venous blood line 50, as will be discussed. It is contemplated that the attachment of venous blood line 50 with proximal end 34 is configured for introduction of fluid into venous lumen 26.

First luer fitting 42 is configured for attachment to venous blood line 50. Venous blood line 50 includes a pusher component 52 that engages first pusher 44 to facilitate fluid communication between venous blood line 50 and venous lumen 26. Venous blood line 50 may be attached via luer connection, threaded connection, snap on, clips, etc.

Venous blood line 50 is attached to first luer fitting 42 such that pusher component 52 engages first pusher 44, causing movement of first pusher 44 in a substantially distal direction, as shown by arrow D. The portion of first pusher 44 protruding from proximal end 34 is engaged by pusher component 52 as venous blood line 50 is attached to proximal end 34. The movement of first pusher 44 causes first valve 38 to overcome the bias of spring 50 and allow movement of first valve 34 in the direction shown by arrow D.

Surface 46 of first valve 38 disengages from surface 48 of proximal end 34. The fluid tight seal is interrupted, thereby opening proximal end 34 to establish fluid communication between proximal end 34 and venous lumen 26.

Conversely, as venous blood line 50 is removed from proximal end 34, pusher component 52 disengages from first pusher 44. Spring 40 re-expands, forcing first valve 38 in the direction shown by arrow C. Surface 46 engages surface 48 to create the fluid tight seal between first valve 38 and proximal end 34. It is contemplated that valve housing 36 may have various geometric configurations such as, rectangular, elliptical, polygonal, etc. It is further contemplated that spring 40 may alternatively include resiliently biasing structure such as, a resilient arm, pneumatic, hydraulic, magnetic force, etc. and may be electronically or manually controlled. First valve 38 may be oriented to engage various portions of proximal end 34. It is envisioned that first valve 38 may be monolithically formed or integrally connected to first pusher 44, or may include other valve structure, such as, slit valves, threaded, umbrella valves, diaphragm valves, etc.

Venous lumen 26 includes a first lateral port 54 disposed adjacent distal end 24 of tubular body 22. First lateral port 54 includes an opening 55 that is configured for fluid flow. First lateral port 54 may be variously dimensioned and configured, such as, for example, rectangular, elliptical, polygonal, etc. Opening 55 is defined by the thickness of a wall portion 56 of tubular body 22 adjacent thereto. First lateral port 54 may include adapters, clips, etc. to facilitate fluid flow and/or attachment to other structure. It is contemplated that first lateral port 54 is configured for expulsion of fluid from venous lumen 26.

Arterial lumen 28 includes a first adapter, such as, for example, tubular arterial adapter 58 that extends to a proximal end 60 thereof. Arterial adapter 58 defines a valve housing 62 adjacent proximal end 60. Valve housing 62 has a cylindrical configuration to facilitate support of a second valve 64 and a spring 66 that biases second valve 64, in a substantially proximal direction as shown by arrow E, to seal proximal end 60. Spring 66 may be fixedly mounted to an inner surface of valve housing 62. A second luer fitting 68 is mounted with proximal end 60. Second luer fitting 68 includes a second pusher 70 that is connected with second valve 64.

It is contemplated that second pusher 70 may be separately formed from second valve 64 and disposed for engagement therewith. It is further contemplated that proximal end 60 is configured for expulsion of fluid to a receiving fluid line. It is envisioned that one or both of lumens 26, 28 may include no adapters, one or a plurality of adapters, such as, for example, an embodiment whereby venous lumen 26 has a valved adapter and arterial lumen 28 does not have a valved adapter.

Spring 66 expands, via a spring force thereof, to engage second valve 64, forcing second valve 64 in the direction shown by arrow E. As second valve 64 moves, a surface 72 of second valve 64 engages a surface 74 of proximal end 60. This engagement creates a fluid tight seal between second valve 64 and proximal end 60. The seal prevents inflow of fluids into arterial lumen 28 and prevents leakage of fluids therefrom. Second valve 64, being connected to second pusher 70, causes second pusher 70 to move in the direction shown by arrow E, and protrude from proximal end 60 for engagement with an arterial blood line 76, as will be discussed.

Second luer fitting 68 is configured for attachment to arterial blood line 76. Arterial blood line 76 includes a pusher component 78 that engages second pusher 70 to facilitate fluid communication between arterial blood line 76 and arterial lumen 26. Arterial blood line 76 may be attached via luer connection, threaded connection, snap on, clips, etc.

Arterial blood line 76 is attached to second luer fitting 68 such that pusher component 78 engages second pusher 70, causing movement of second pusher 70 in a substantially distal direction, as shown by arrow F. The portion of second pusher 70 protruding from proximal end 60 is engaged by pusher component 70 as arterial blood line 76 is attached to proximal end 60. The movement of second pusher 70 causes second valve 64 to overcome the bias of spring 66 and allow movement of second valve 64 in the direction shown by arrow F.

Surface 72 of second valve 64 disengages from surface 74 of proximal end 60. The fluid tight seal is interrupted, thereby opening proximal end 60 to establish fluid communication between proximal end 60 and arterial lumen 28.

Conversely, as arterial blood line 76 is removed from proximal end 60, pusher component 78 disengages from second pusher 70. Spring 66 re-expands, forcing second valve 64 in the direction shown by arrow E. Surface 72 engages surface 74 to create the fluid tight seal between second valve 64 and proximal end 60. It is contemplated that valve housing 62 may have various geometric configurations such as, rectangular, elliptical, polygonal, etc. It is further contemplated that spring 66 may alternatively include resiliently biasing structure such as, a resilient arm, pneumatic, hydraulic, magnetic force, etc. and may be electronically or manually controlled. Second valve 64 may be oriented to engage various portions of proximal end 60. It is envisioned that second valve 64 may be monolithically formed or integrally connected to second pusher 70, or may include other valve structure, such as, slit valves, threaded, umbrella valves, diaphragm valves, etc.

Arterial lumen 28 includes a second lateral port 80 disposed adjacent distal end 24 of tubular body 22. Second lateral port 80 includes an opening 82 that is configured for fluid flow. Opening 82 may be variously dimensioned and configured, such as, for example, rectangular, elliptical, polygonal, etc. Opening 82 is defined by the thickness of a wall portion 84 of tubular body 22 adjacent thereto. Second lateral port 80 may include adapters, clips, etc. to facilitate fluid flow and/or attachment to other structure. It is contemplated that second lateral port 80 is configured for introduction of fluid into arterial lumen 28.

A push rod 88 is connected to first valve 38 within valve housing 36. Push rod 88 is slidably supported by a central lumen 90 (FIG. 3A) of tubular body 22 and extends to a pointed distal tip 92 disposed adjacent distal end 24. Central lumen 90 is disposed between venous lumen 26 and arterial lumen 28, and extends to distal end 24. Push rod 88 is mounted with central lumen 90 such that the portion of push rod 88 disposed with venous adapter 32 is coaxially mounted therewith.

Push rod 88 is associated with first valve 38 for corresponding slidable movement therewith. For example, as first valve 38 is forced proximally in the direction shown by arrow C, discussed above, push rod 88 is similarly forced in the direction shown by arrow C. Further, as first valve 38 is forced distally in the direction shown by arrow D, discussed above, push rod 88 is similarly forced in the direction shown by arrow D. Tip 92 is movable corresponding to the movement of first valve 38, as facilitated by push rod 88. The slidable movement of push rod 88 causes corresponding slidable movement of a valve 94 that includes tip 92, as will be discussed.

Tip 92 has a proximal portion 96 and a distal portion 98. Proximal portion 96 includes a first member 100 extending into venous lumen 26 and a second member 102 extending into arterial lumen 28. First lateral port 54 is disposed proximally, with tubular body 22, relative to second lateral port 80. Thus, first member 100 extends a greater dimensional length than second member 102 to seal first lateral port 54 and second lateral port 80, as will be discussed.

First member 100 extends, in a proximal direction, a greater depth within venous lumen 26 relative to the depth of extension of second member 102 within arterial lumen 28. It is envisioned that second member 102 may extend a greater depth within lumens 26, 28 than first member 100, or alternatively, first member 100 and second member 102 may extend the same depth.

First member 100 includes an arcuate portion 104 that conforms to the correspondingly configured arcuate portion 27B of inner surface 27 of venous lumen 26, adjacent first lateral port 54. Arcuate portion 104 engages arcuate portion 27B to facilitate slidable movement of first member 100 relative to venous lumen 26. It is contemplated that arcuate portion 104 sealingly engages arcuate portion 27B via interference using an O-ring type thin malleable surface, an umbrella type valve surface, etc. It is envisioned that first member 100 may have a D-shaped/semicircular cross-section, or may have a wall portion that includes arcuate portion 104.

Second member 102 includes an arcuate portion 106 that conforms to the correspondingly configured arcuate portion 29B of inner surface 29 of arterial lumen 28, adjacent second lateral port 80. Arcuate portion 106 engages arcuate portion 29B to facilitate slidable movement of second member 102 relative to arterial lumen 28. It is envisioned that arcuate position 106 sealingly engages arcuate portion 29B via interference using an O-ring type thin malleable surface, an umbrella type valve surface, etc. It is contemplated that second member 102 may have a D-shaped/semicircular cross-section, or may have a wall portion that includes arcuate portion 106. It is further contemplated that first member 100 and second member 102 may be monolithically formed with tip 92, or alternatively, may be integrally assembled with tip 92 and fabricated from dissimilar materials.

Distal portion 98 of tip 92 includes a pointed distal head 99. Distal head 99 facilitates disposal of tubular body 22 within a body vessel and may be employed with a guidewire, sheath, etc. It is envisioned that distal head 99 may be employed with a stylet, tunneler, trocar, etc. to tunnel tubular body 22 under the skin of a subject (not shown). It is contemplated that distal head 99 may be variously configured or, alternatively, distal portion 98 may include a blunt tip. It is contemplated that tip 92 allows for aspiration through an angle of 360 degrees. This configuration facilitates disposal of distal end 24 of tubular body 22 in a plurality of orientations and prevents positional occlusion.

As push rod 88 moves distally, as shown by arrow C, or proximally, as shown by arrow D, first member 100 and second member 102, extending from tip 92, similarly move in a distal direction and a proximal direction. Such movement facilitates corresponding movement of valve 94, which includes tip 92, between a closed position (FIG. 3) and an open position (FIG. 4).

In the closed position, tip 92 flushly engages distal end 24 of tubular body 22. First member 100 extends a sufficient depth within venous lumen 26 such that arcuate portion 104 spans across first lateral port 54. Arcuate portion 104 flushly engages first lateral port 54 and the adjacent portions of arcuate portion 27B of venous lumen 26 to close off first lateral port 54 and create a fluid tight seal therewith. Similarly, second member 102 extends a sufficient depth within arterial lumen 28 such that arcuate portion 106 spans across second lateral port 80. Arcuate portion 106 flushly engages second lateral port 80 and the adjacent portions of arcuate portion 29B of arterial lumen 28 to close of second lateral port 80 and create a fluid tight seal therewith.

As push rod 88 moves in the distal direction, as shown by arrow D, first member 100 and second member 102 are caused to slidably move relative to venous lumen 26 and arterial lumen 28, respectively. First member 100 slides out of alignment with first lateral port 54. Second member 102 slides out of alignment with second lateral port 80.

In the open position, first member 100 disengages from first lateral port 54 and the adjacent portions of arcuate portion 27B of venous lumen 26 to interrupt and open the fluid tight seal of first lateral port 54, thereby facilitating fluid communication between first lateral port 54 and venous lumen 26.

Similarly, second member 102 disengages from second lateral port 80 and the adjacent portions of arcuate portion 29B of arterial lumen 28 to interrupt and open the fluid tight seal of second lateral port 80, thereby facilitating fluid communication between second lateral port 80 and arterial lumen 28.

As push rod 88 is caused to move back in the proximal direction, as shown by arrow C, first member 100 and second member 102 are caused to slidably move relative to venous lumen 26 and arterial lumen 28, respectively. First member 100 reseals first lateral port 54, as discussed, and second member 102 reseals second lateral port 80, as discussed, such that valve 94, which includes tip 92, is again disposed in the closed position. It is contemplated that valve 94, including tip 92, may be releasably locked or permanently fixed in the open position and/or the closed position via detents, clips, etc. mounted adjacent distal end 24, adapters 32, 58 or along other portions of tubular body 22. This configuration advantageously facilitates desirable fluid flow rates and may break up thrombus or fibrin sheath formation. Further, the structure and methods illustrated for achieving the principles of the present disclosure also advantageously prevent undesirable fluid evacuation to further prevent thrombus formation on an innersurface of tubular body 22.

Figure 3:
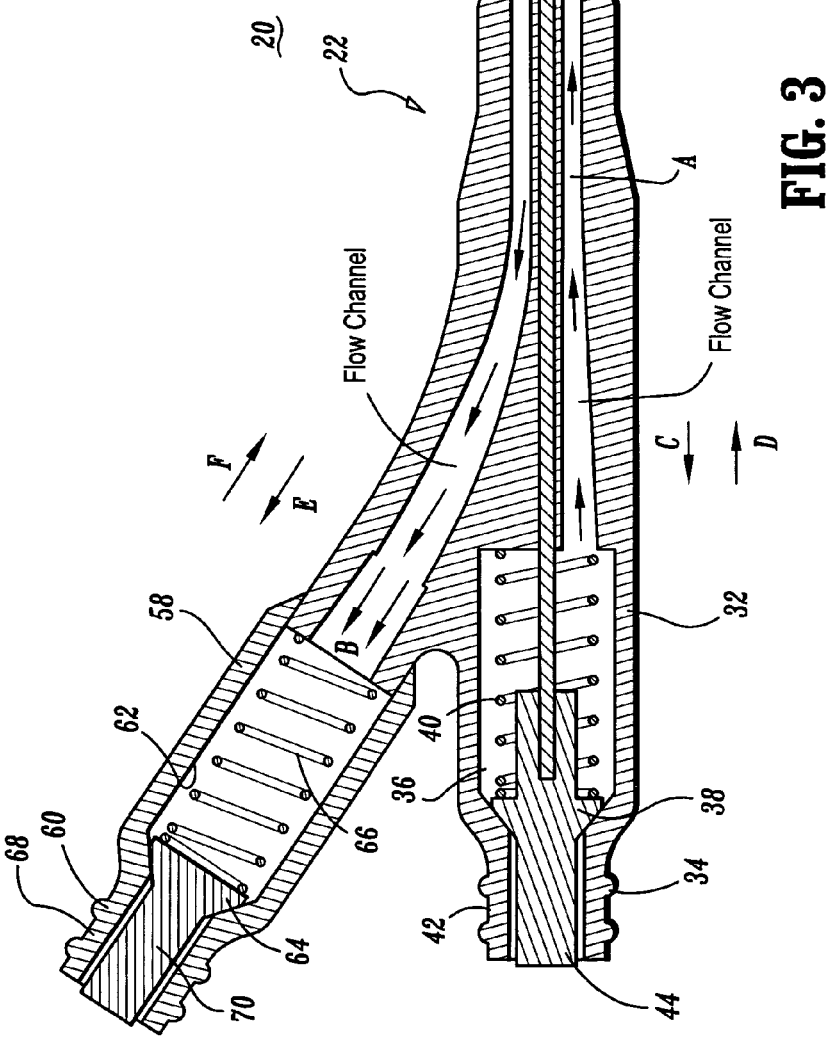
FIG. 3 is a side cross-sectional view, in part elevation, of the catheter apparatus in a closed position taken along line A—A of FIG. 2.
Figure 4:
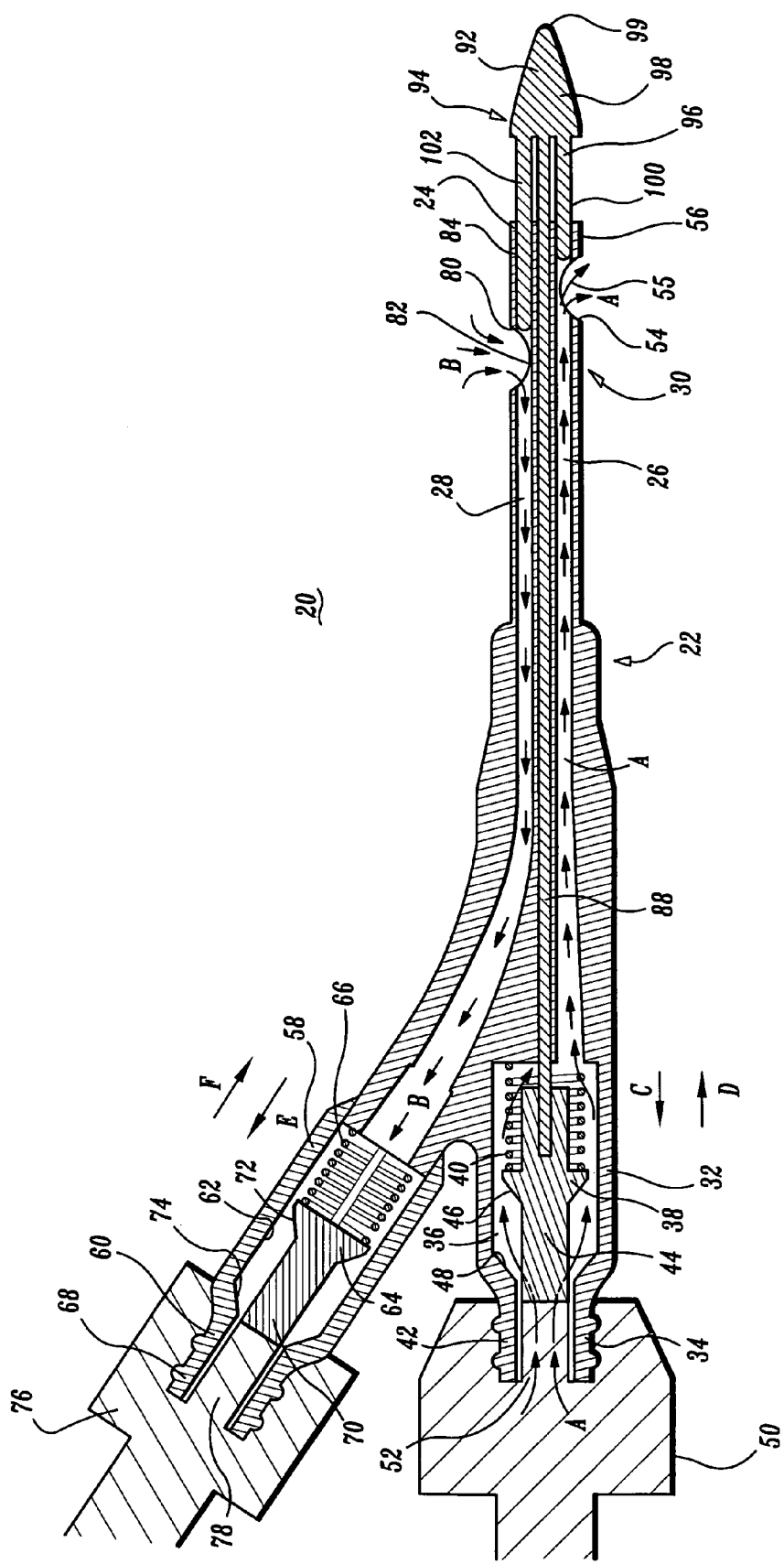
FIG. 4 is an a side cross-sectional view, in part elevation, of the catheter apparatus in an open position taken along line A—A of FIG. 2.
Figure 5:
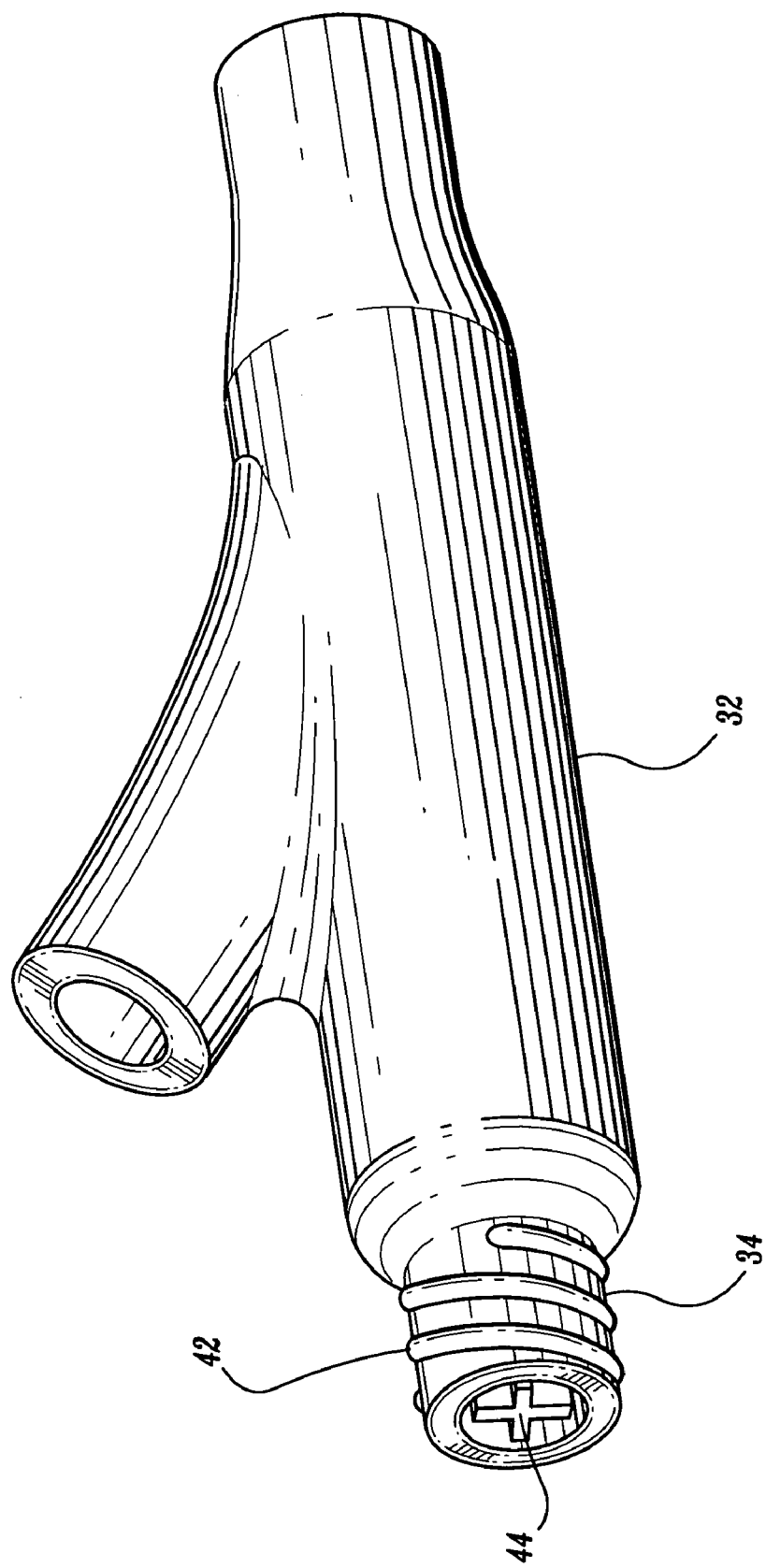
FIG. 5 is an enlarged perspective cutaway view of a proximal end of the catheter apparatus.
Figure 6:
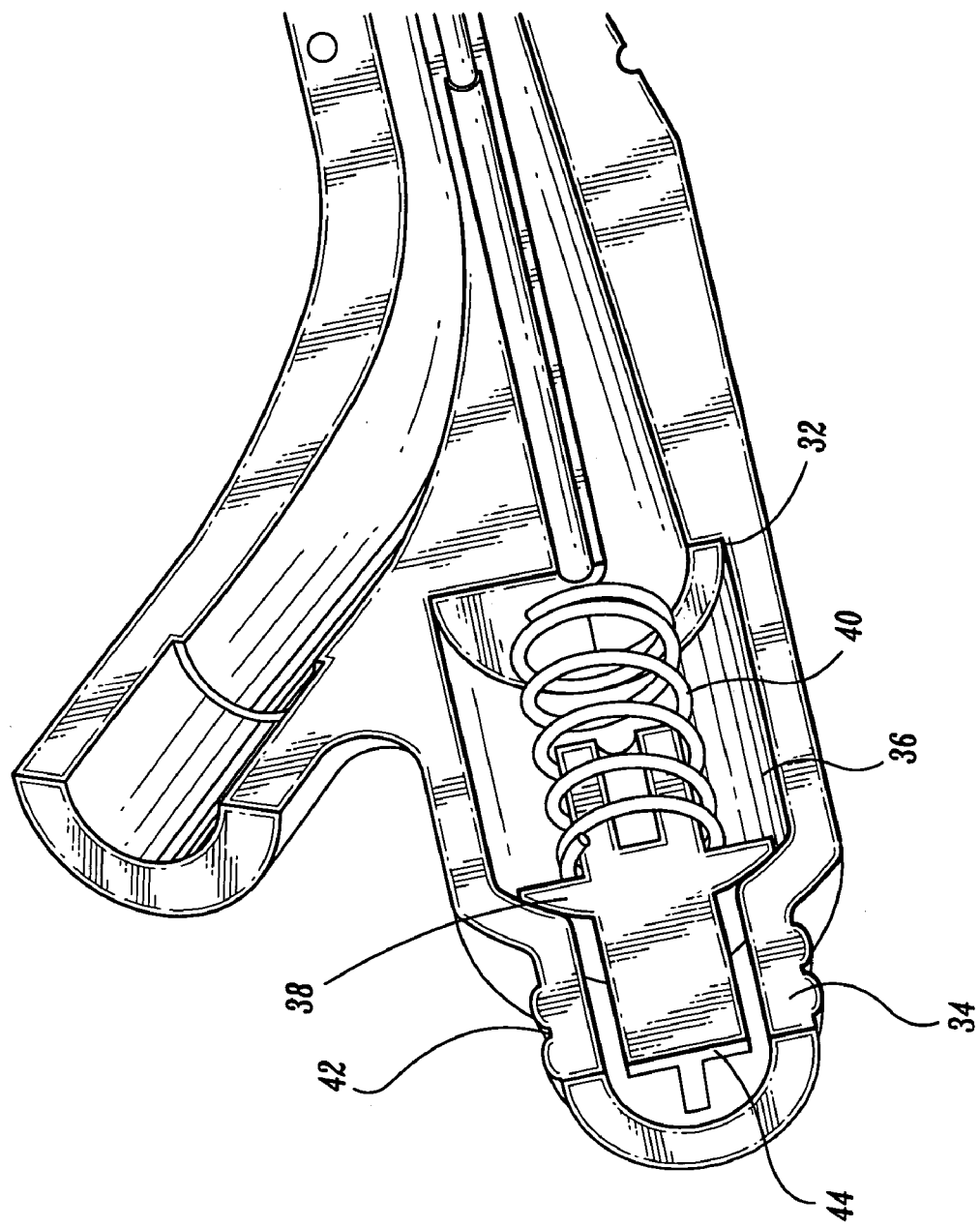
FIG. 6 is a perspective half-section view of the proximal end shown in FIG. 5 in a sealed configuration.
Figure 7:
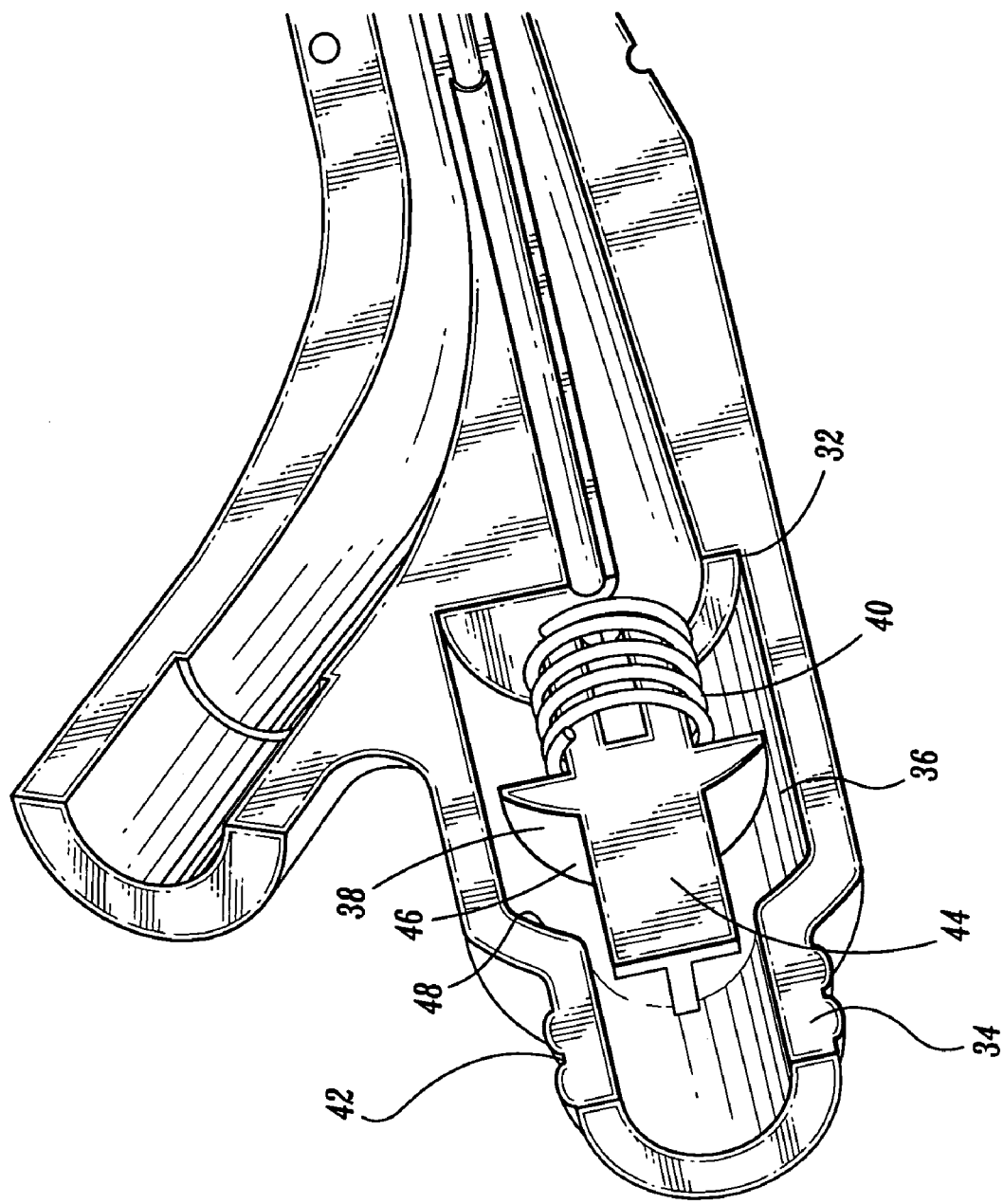
FIG. 7 is a perspective half-section view of the proximal end shown in FIG. 5 in a non-sealed configuration.
Figure 8:
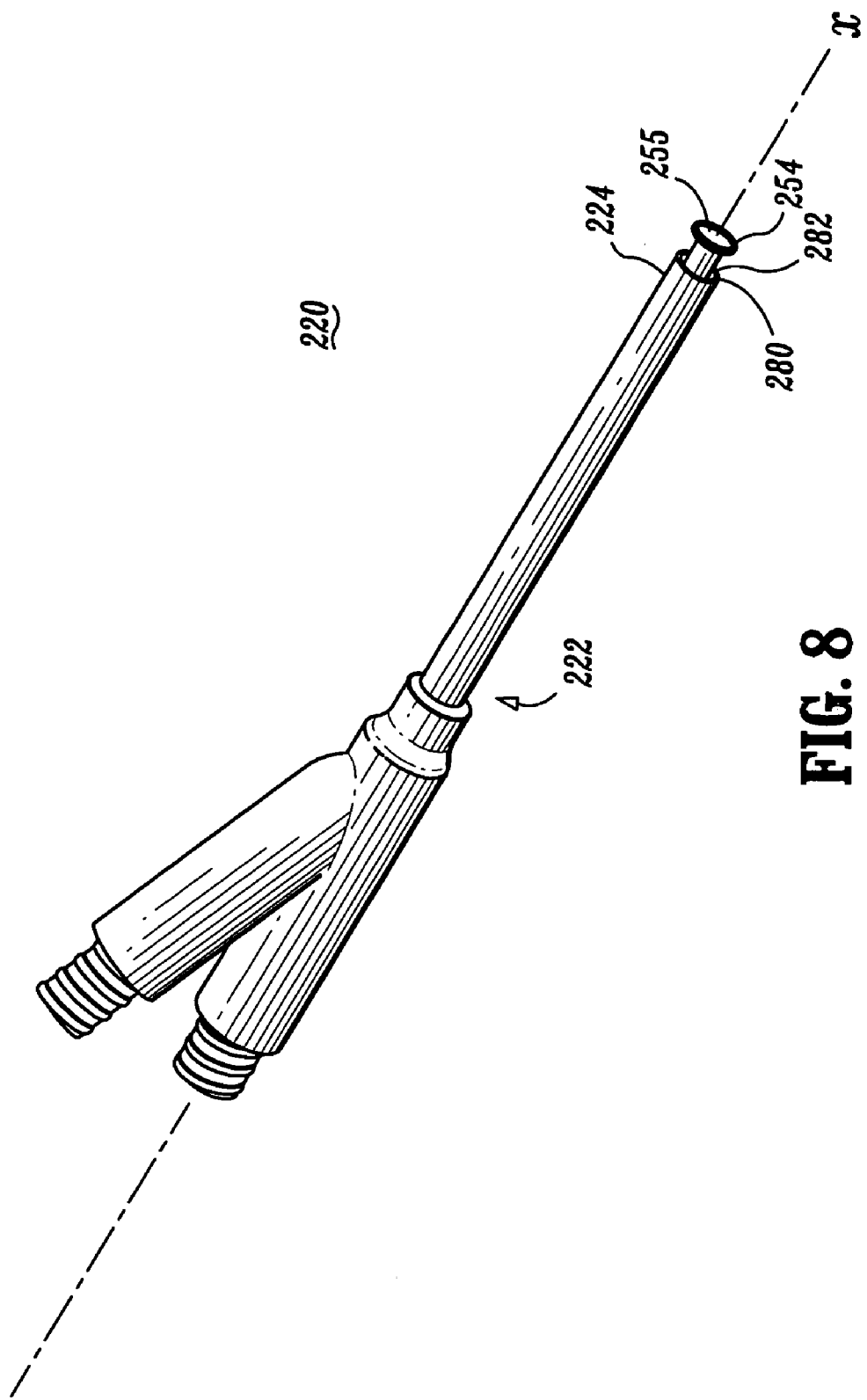
FIG. 8 is a perspective view of an alternate embodiment of the catheter apparatus, in accordance with the principles of the present disclosure.
Figure 9:
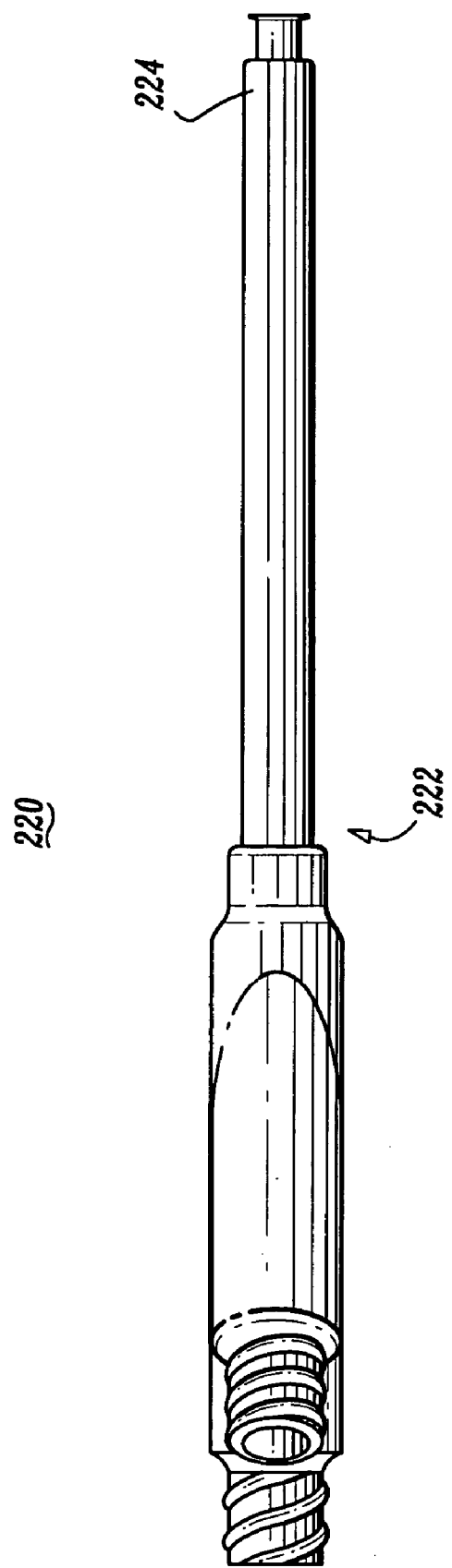
FIG. 9 is a top perspective view of the catheter apparatus shown in FIG. 8.
Figure 10:
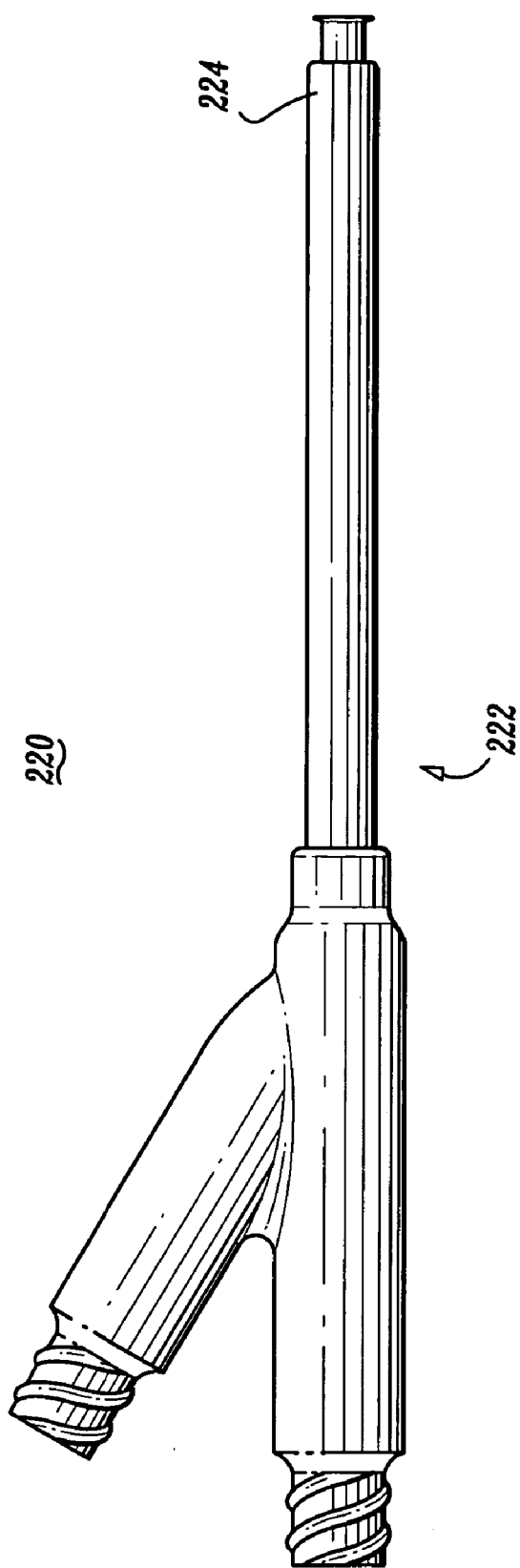
FIG. 10 is a side view of the catheter apparatus shown in FIG. 8.
Figure 11:
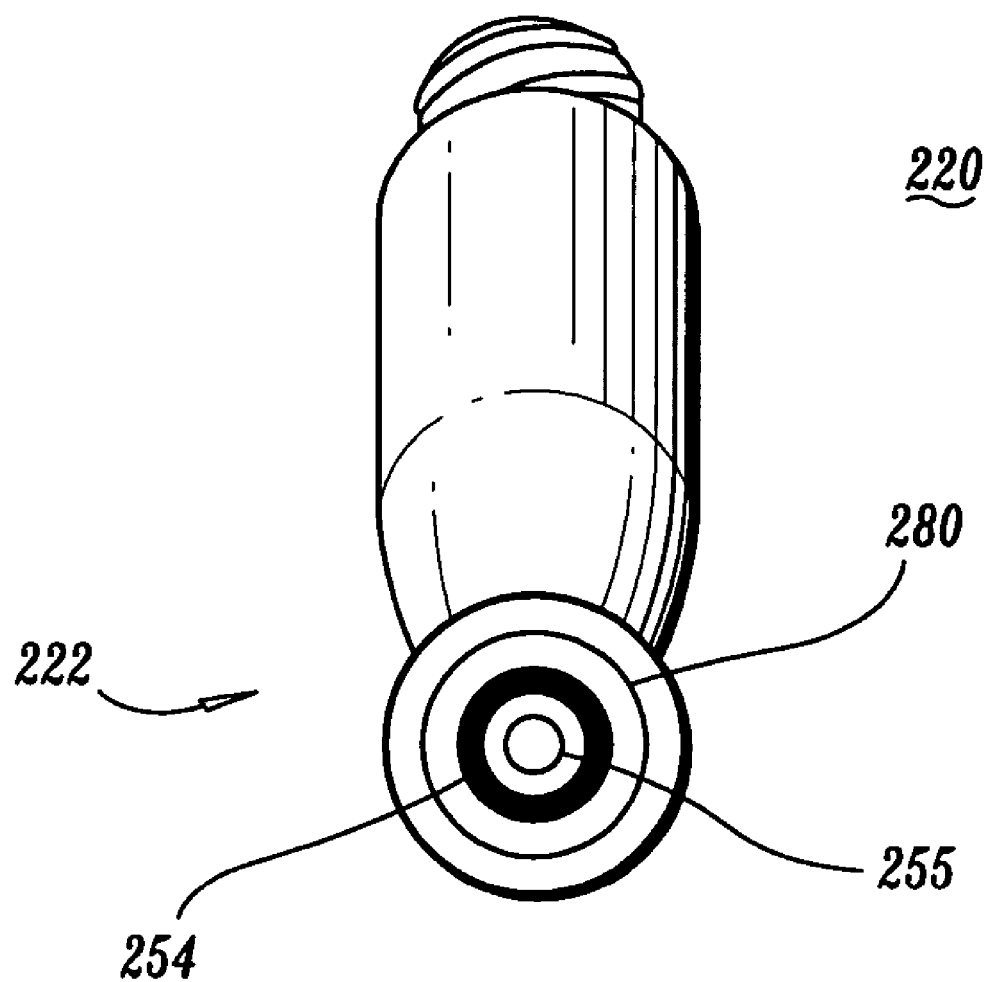
FIG. 11 is a front view of the catheter apparatus shown in FIG. 8.

Referring to FIGS. 3 and 4, in use, a catheter apparatus 20, similar to that described, is assembled, properly sterilized and otherwise prepared for storage, shipment and use in a hemodialysis procedure. A practitioner (not shown) manipulates distal end 24 of tubular body 22 such that pointed distal head 99 of tip 92 can enter a body cavity of a subject (not shown). Distal end 24 is inserted within a blood vessel of the subject. Catheter apparatus 20 is employed for administration of fluids that includes the simultaneous introduction of venous blood flow and withdrawal of arterial blood flow. Catheter apparatus 20 is inserted with the blood vessel of the subject such that blood is withdrawn, via arterial blood flow in a first direction, from the blood vessel for treatment by an artificial kidney device (not shown) and the treated blood is introduced back into the blood vessel, via venous blood flow in a second opposite direction.

Initially, valve 94, which includes tip 92, is in the closed position. First member 100 extends within venous lumen 26 such that arcuate portion 104 spans across first lateral port 54. Arcuate portion 104 flushly engages first lateral port 54 and the adjacent portions of arcuate portion 27B of venous lumen 26 to close off first lateral port 54 and create a fluid tight seal therewith. Similarly, second member 102 extends within arterial lumen 28 such that arcuate portion 106 spans across second lateral port 80. Arcuate portion 106 flushly engages second lateral port 80 and the adjacent portions of arcuate portion 29B of arterial lumen 28 to close of second lateral port 80 and create a fluid tight seal therewith.

Surface 46 of first valve 38 engages surface 48 of proximal end 34 to create a fluid tight seal between first valve 38 and proximal end 34, as discussed. First pusher 44 protrudes from proximal end 34. Surface 72 of second valve 64 engages surface 74 of proximal end 60 to create a fluid tight seal between second valve 64 and proximal end 60. Second pusher 70 protrudes from proximal end 60.

Venous blood line 50 is attached to first luer fitting 42 such that pusher component 52 engages first pusher 44, causing movement of first pusher 44 in a substantially distal direction, as shown by arrow D, overcoming the bias of spring 50. Surface 46 of first valve 38 disengages from surface 48 of proximal end 34 and the fluid tight seal is interrupted, thereby opening proximal end 34 to establish fluid communication between proximal end 34 and venous lumen 26. Venous blood flow is introduced to catheter apparatus 20 through proximal end 34.

Arterial blood line 76 is attached to second luer fitting 68 such that pusher component 78 engages second pusher 70, causing movement of second pusher 70 in a substantially distal direction, as shown by arrow F, overcoming the bias of spring 66. Surface 72 of second valve 64 disengages from surface 74 of proximal end 60 and the fluid tight seal is interrupted, thereby opening proximal end 60 to establish fluid communication between proximal end 60 and arterial lumen 28. Arterial blood flow may be received by arterial blood line 76.

As first valve 38 is forced distally in the direction shown by arrow D, discussed above, push rod 88 is similarly forced in the direction shown by arrow D. Valve 94, which includes tip 92, is movable corresponding to the movement of first valve 38, as facilitated by push rod 88. As push rod 88 moves in the distal direction, first member 100 and second member 102 are caused to slidably move relative to venous lumen 26 and arterial lumen 28, respectively. First member 100 slides out of alignment with first lateral port 54. Second member 102 slides out of alignment second lateral port 80.

Valve 94, which includes tip 92, moves to the open position. First member 100 disengages from first lateral port 54 and the adjacent portions of arcuate portion 27B of venous lumen 26 to interrupt and open the fluid tight seal of first lateral port 54, thereby facilitating fluid communication between first lateral port 54 and venous lumen 26. Thus, venous blood flow is introduced to the blood vessel of the subject via venous lumen 26. Second member 102 disengages from second lateral port 80 and the adjacent portions of arcuate portion 29B of arterial lumen 28 to interrupt and open the fluid tight seal of second lateral port 80, thereby facilitating fluid communication between second lateral port 80 and arterial lumen 28. Thus, arterial blood flow is withdrawn from the blood vessel and received by arterial lumen 28 for receipt by arterial blood line 76.

In the event that the practitioner desires to discontinue administration of fluids with the subject, valve 94, which includes tip 92, may be returned to the closed position. Venous blood line 50 is removed from proximal end 34 to recreate the fluid tight seal between first valve 38 and proximal end 34. Arterial blood line 76 is removed from proximal end 60 to recreate the fluid tight seal between second valve 64 and proximal end 60.

Push rod 88 is caused to move back in the proximal direction, as shown by arrow C. First member 100 reseals first lateral port 54 and second member 102 reseals second lateral port 80 such that valve 94, which includes tip 92, is again disposed in the closed position.

Referring to FIGS. 8–13, an alternate embodiment of the present disclosure is shown that includes a catheter apparatus 220. Catheter apparatus 220 includes a tubular body 222 having a distal end 224. Tubular body 222 is elongated and has a cylindrical outer surface.

Tubular body 222 defines a first lumen such as, for example, venous lumen 226 and a second lumen such as, for example, arterial lumen 228. Venous lumen 226 and arterial lumen 228 are in a substantially coaxial orientation, with a longitudinal axis x, along a distal portion 230 of tubular body 222. Venous lumen 226 and arterial lumen 228 each have a substantially tubular configuration that facilitate fluid flow. It is envisioned that lumens 226, 228 may have various configurations, such as, for example, cylindrical, rectangular, elliptical, polygonal, etc.

Venous lumen 226 is configured for fluid flow, such as, for example, venous blood flow, in a first direction, as shown by arrows AA. Arterial lumen 228 is configured for fluid flow, such as, for example, arterial blood flow in a second opposite direction, as shown by arrows BB. The first and second lumens may be configured for various forms of fluid flow in various directions and orientations, according to the requirements of a particular catheter application.

Lumens 226, 228 may be uniformly dimensioned or include alternative dimensional cross sections within tubular body 222, such as, narrow and broad portions, converging surfaces, undulating surfaces, etc. according to the particular flow indications and/or flow rate requirements. It is contemplated venous lumen 226 and arterial lumen 228 may extend alternative lengths. It is further contemplated that tubular body 222 may include one or a plurality of lumens. It is envisioned that the first lumen may include the arterial lumen and the second lumen may include the venous lumen.

Venous lumen 226 includes a first adapter, such as, for example, tubular venous adapter 232 that extends to a proximal end 234 thereof. Venous adapter 232 defines a valve housing 236 adjacent proximal end 234. Valve housing 236 has a cylindrical configuration to facilitate support of a first valve 238 and a spring 240 that biases first valve 238, in a substantially proximal direction as shown by arrow CC, to seal proximal end 234. Spring 240 may be fixedly mounted to an inner surface of valve housing 236. A first luer fitting 242 is mounted with proximal end 234. First luer fitting 242 includes a first pusher 244 that is connected with first valve 238.

Spring 240 expands, via a spring force thereof, to engage first valve 238, forcing first valve 238 in the direction shown by arrow CC. As first valve 238 moves, a surface 246 of first valve 238 engages a surface 248 of proximal end 234. This engagement creates a fluid tight seal between first valve 238 and proximal end 234. The seal prevents inflow of fluids into venous lumen 226 and prevents leakage of fluids therefrom. First valve 238, being connected to first pusher 244, causes first pusher 244 to move in the direction shown by arrow CC, and protrude from proximal end 234 for engagement with a venous blood line 250, as will be discussed.

First luer fitting 242 is configured for attachment to venous blood line 250. Venous blood line 250 includes a pusher component 252 that engages first pusher 244 to facilitate fluid communication between venous blood line 250 and venous lumen 226.

Venous blood line 250 is attached to first luer fitting 242 such that pusher component 252 engages first pusher 244, causing movement of first pusher 244 in a substantially distal direction, as shown by arrow DD. The portion of first pusher 244 protruding from proximal end 234 is engaged by pusher component 252 as venous blood line 250 is attached to proximal end 234. The movement of first pusher 244 causes first valve 238 to overcome the bias of spring 250 and allow movement of first valve 234 in the direction shown by arrow DD.

Surface 246 of first valve 238 disengages from surface 248 of proximal end 234. The fluid tight seal is interrupted, thereby opening proximal end 234 to establish fluid communication between proximal end 234 and venous lumen 226. Conversely, as venous blood line 250 is removed from proximal end 234, pusher component 252 disengages from first pusher 244. Spring 240 re-expands, forcing first valve 238 in the direction shown by arrow CC. Surface 246 engages surface 248 to create the fluid tight seal between first valve 238 and proximal end 234.

Venous lumen 226 defines a first port 254 disposed adjacent distal end 224 of tubular body 222. First port 254 includes an opening 255 that is configured for fluid flow. First port 254 may be variously dimensioned and configured, such as, for example, rectangular, elliptical, polygonal, etc. First port 254 may include adapters, clips, etc. to facilitate fluid flow and/or attachment to other structure. It is contemplated that first port 254 is configured for expulsion of fluid from venous lumen 226.

Arterial lumen 228 includes a first adapter, such as, for example, tubular arterial adapter 258 that extends to a proximal end 260 thereof. Arterial adapter 258 defines a valve housing 262 adjacent proximal end 260. Valve housing 262 has a cylindrical configuration to facilitate support of a second valve 264 and a spring 266 that biases second valve 264, in a substantially proximal direction as shown by arrow EE, to seal proximal end 260. Spring 266 may be fixedly mounted to an inner surface of valve housing 262. A second luer fitting 268 is mounted with proximal end 260. Second luer fitting 268 includes a second pusher 270 that is connected with second valve 264.

Spring 266 expands, via a spring force thereof, to engage second valve 264, forcing second valve 264 in the direction shown by arrow EE. As second valve 264 moves, a surface 272 of second valve 264 engages a surface 274 of proximal end 260. This engagement creates a fluid tight seal between second valve 264 and proximal end 260. The seal prevents inflow of fluids into arterial lumen 228 and prevents leakage of fluids therefrom. Second valve 264, being connected to second pusher 270, causes second pusher 270 to move in the direction shown by arrow EE, and protrude from proximal end 260 for engagement with an arterial blood line 276, as will be discussed. Second luer fitting 268 is configured for attachment to arterial blood line 276. Arterial blood line 276 includes a pusher component 278 that engages second pusher 270 to facilitate fluid communication between arterial blood line 276 and arterial lumen 226.

Arterial blood line 276 is attached to second luer fitting 268 such that pusher component 278 engages second pusher 270, causing movement of second pusher 270 in a substantially distal direction, as shown by arrow FF. The portion of second pusher 270 protruding from proximal end 260 is engaged by pusher component 270 as arterial blood line 276 is attached to proximal end 260. The movement of second pusher 270 causes second valve 264 to overcome the bias of spring 266 and allow movement of second valve 264 in the direction shown by arrow FF.

Surface 272 of second valve 264 disengages from surface 274 of proximal end 260. The fluid tight seal is interrupted, thereby opening proximal end 260 to establish fluid communication between proximal end 260 and arterial lumen 228. Conversely, as arterial blood line 276 is removed from proximal end 260, pusher component 278 disengages from second pusher 270. Spring 266 re-expands, forcing second valve 264 in the direction shown by arrow EE. Surface 272 engages surface 274 to create the fluid tight seal between second valve 264 and proximal end 260.

Arterial lumen 228 includes a second port 280 disposed adjacent distal end 224 of tubular body 222. Second port 280 includes an opening 282 that is configured for fluid flow. Opening 282 may be variously dimensioned and configured, such as, for example, rectangular, elliptical, polygonal, etc. Second port 280 may include adapters, clips, etc. to facilitate fluid flow and/or attachment to other structure. It is contemplated that second port 280 is configured for introduction of fluid into arterial lumen 228.

A portion of venous lumen 226, such as, for example, push rod portion 288 is connected to first valve 238 within valve housing 236 for corresponding movement therewith. Push rod portion 288 is slidably mounted within tubular body 222 and extends to first port 254. First port 254 seals second port 280 in a closed position of a valve configuration including first port 254 and second port 280.

Push rod portion 288 is connected with first valve 238 for corresponding slidable movement therewith. Push rod portion 288 includes openings 289 that facilitate fluid communication between proximal end 234 and venous lumen 226. Openings 289 may be variously configured such as, slots, vents, circular, polygonal, etc. Push rod portion 288 may be attached to first valve 238 by various means, such as, for example, adhesive, clips, etc., may be monolithic therewith, or spaced apart therefrom.

For example, as first valve 238 is forced proximally in the direction shown by arrow CC, discussed above, push rod portion 288 is similarly forced in the direction shown by arrow CC. Further, as first valve 238 is forced distally in the direction shown by arrow DD, discussed above, push rod portion 288 is similarly forced in the direction shown by arrow DD. First port 254 is movable corresponding to the movement of first valve 238, as facilitated by push rod portion 288.

As push rod portion 288 moves proximally, as shown by arrow CC, or distally, as shown by arrow DD, first port 254 similarly moves in a proximal direction and a distal direction. Such movement facilitates corresponding movement of the valve configuration that includes first port 254 and second port 280, between a closed position (FIG. 12) and an open position (FIG. 13).

In the closed position, first port 254 engages second port 280 to close off second port 280 and create a fluid tight seal therewith. As push rod portion 288 moves in the distal direction, as shown by arrow DD, first port 254 is caused to slidably move relative to distal end 224 and second port 280. In the open position, first port 254 disengages from second port 280 to interrupt and open the fluid tight seal of second port 280, thereby facilitating fluid communication between second port 280 and arterial lumen 228.

As push rod portion 288 is caused to move back in the proximal direction, as shown by arrow CC, first port 254 is caused to slidably move relative to distal end 224 and second port 280. First port 254 reseals second port 280, as discussed, such that the valve configuration that includes first port 254 and second port 280 is again disposed in the closed position. It is contemplated that the valve configuration that includes first port 254 and second port 280 may be releasably locked or permanently fixed in the open position and/or the closed position via detents, clips, etc. mounted adjacent distal end 224, adapters 232, 258 or along other portions of tubular body 222. This configuration advantageously facilitates desirable fluid flow rates and may prevent thrombosis and fibrin sheath formation. Further, the structure and methods illustrated for achieving the principles of the present disclosure also advantageously prevent undesirable fluid evacuation and enhance comfort to a subject. It is envisioned that one or both of lumens 226, 228 may include no adapters, one or a plurality of adapters, such as, for example, an embodiment whereby venous lumen 226 has a valved adapter and arterial lumen 228 does not have a valved adapter.

Figure 12:
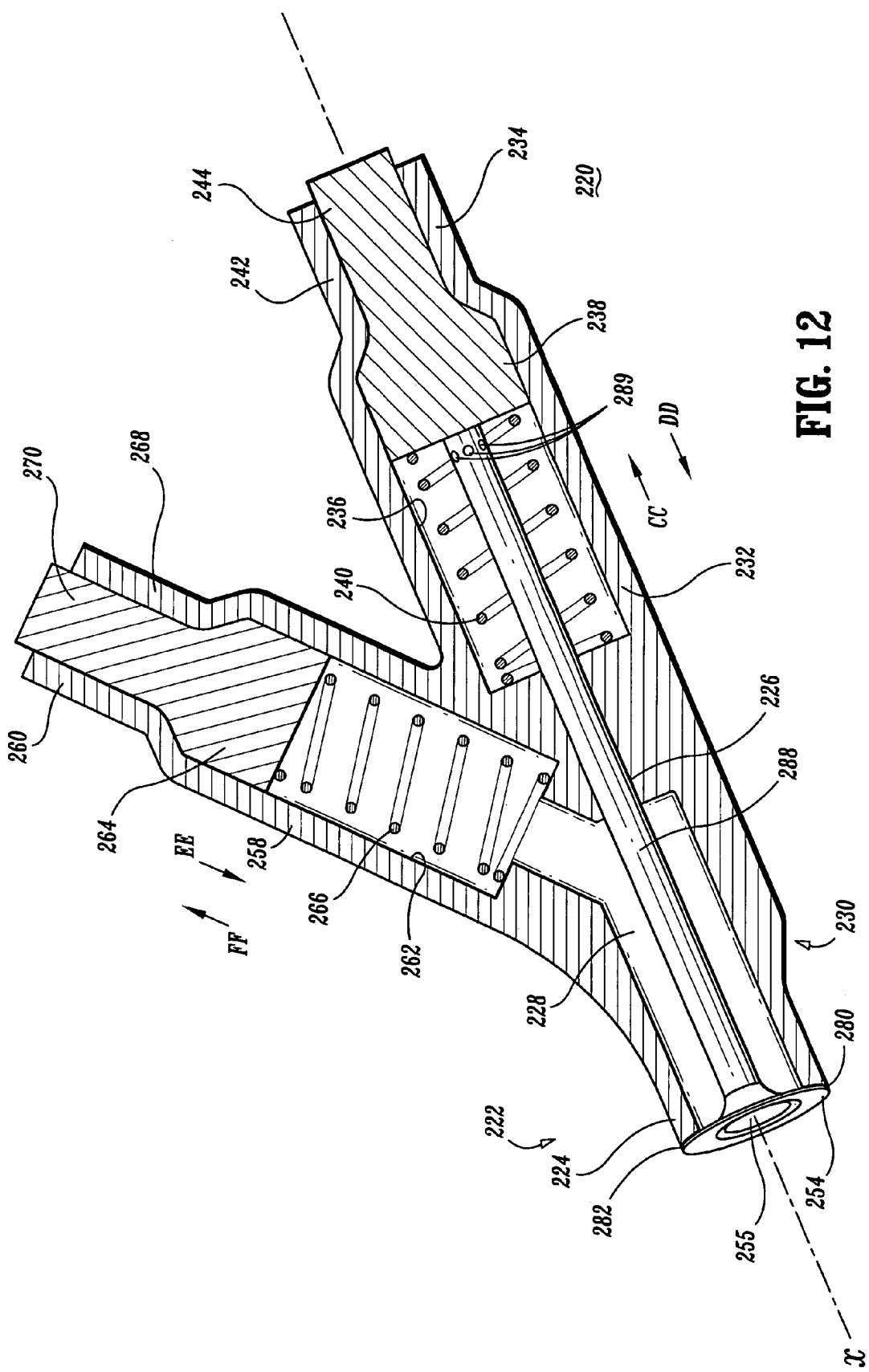
FIG. 12 is an enlarged perspective half section view of the catheter apparatus shown in FIG. 8, in a closed position.
Figure 13:
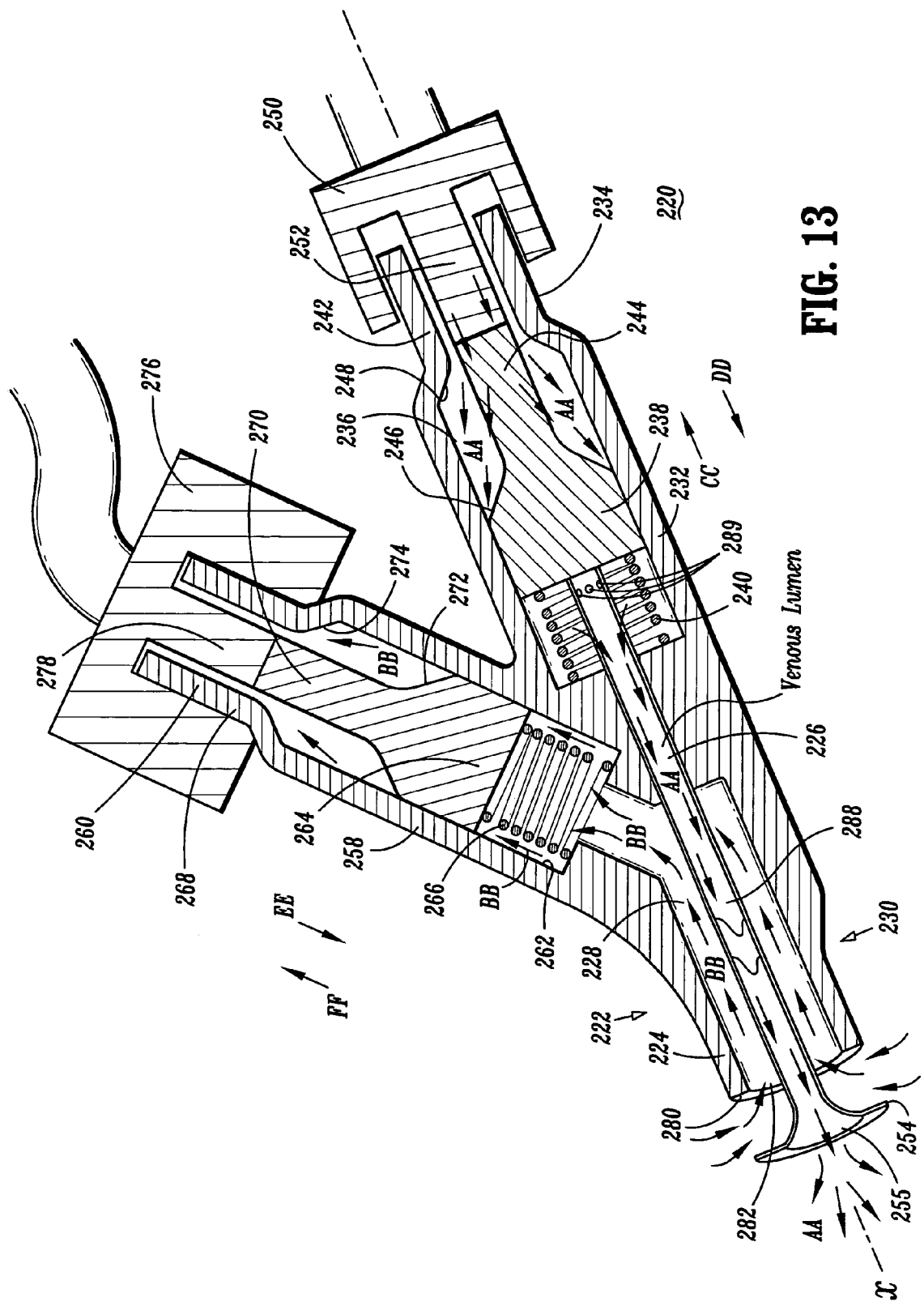
FIG. 13 is an enlarged perspective half section view of the catheter apparatus shown in FIG. 8, in an open position.
Figure 14:
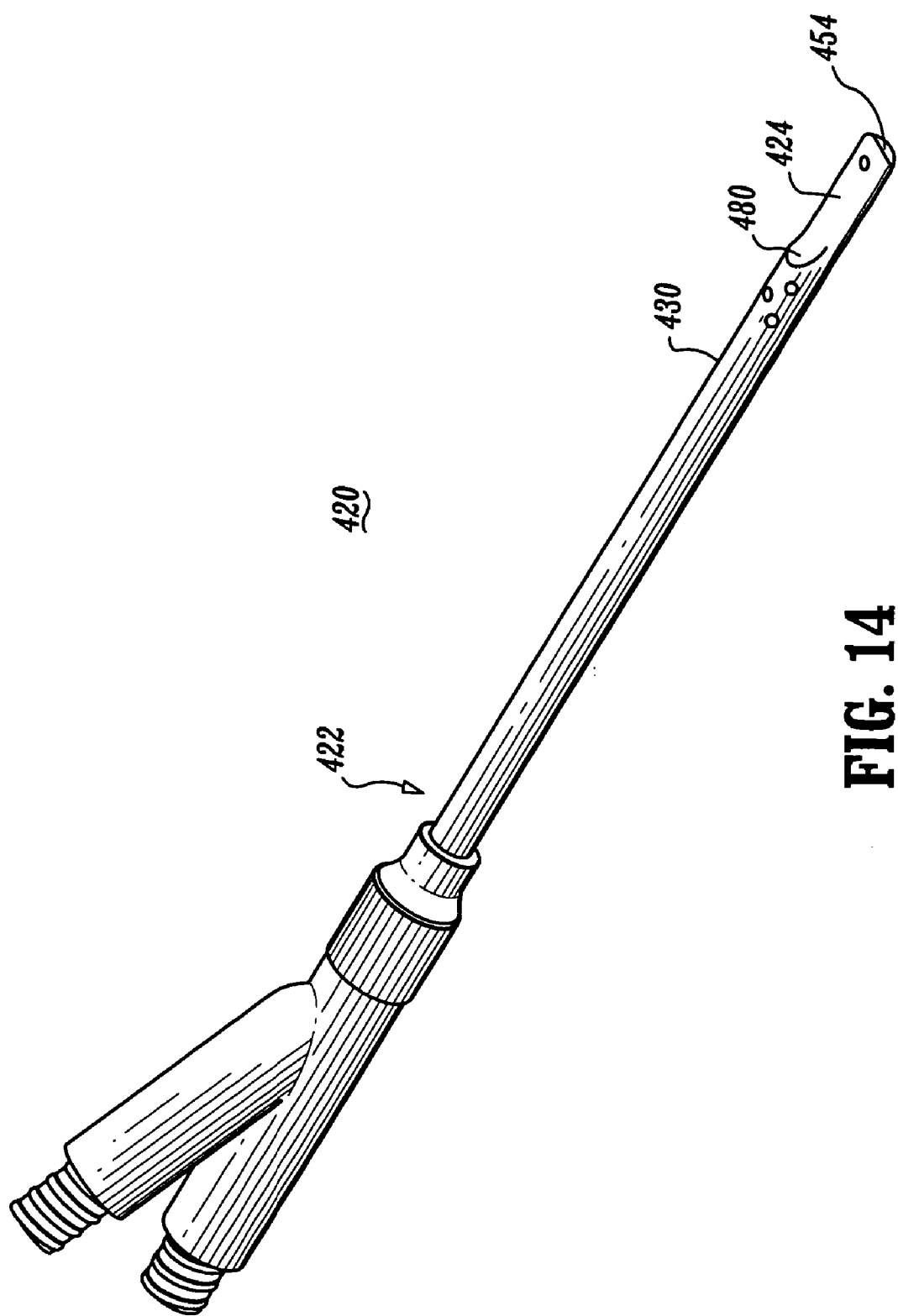
FIG. 14 is a perspective view of another alternate embodiment of the catheter apparatus, in accordance with the principles of the present disclosure.
Figure 15:
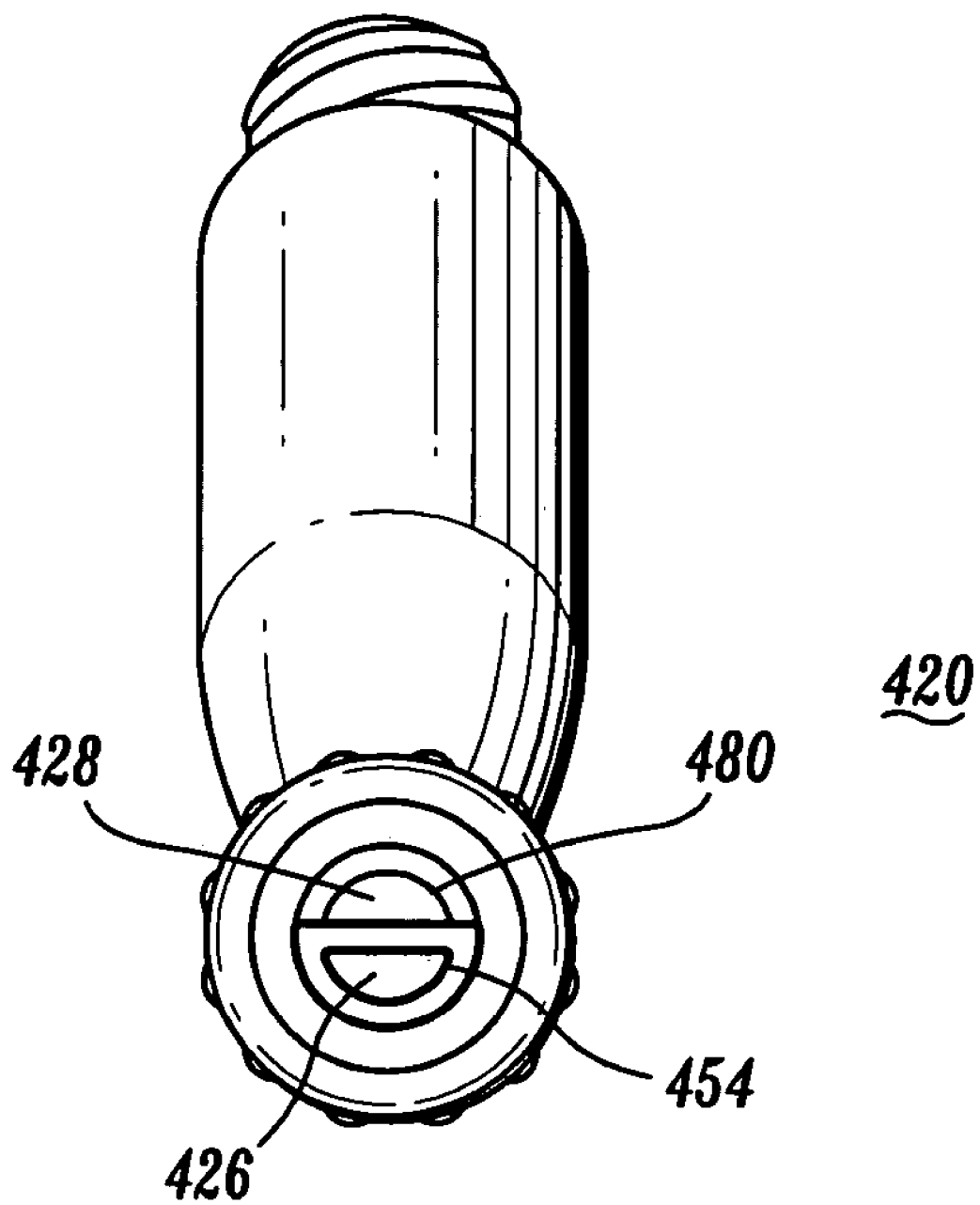
FIG. 15 is a front view of the catheter apparatus shown in FIG. 14.
Figure 16:
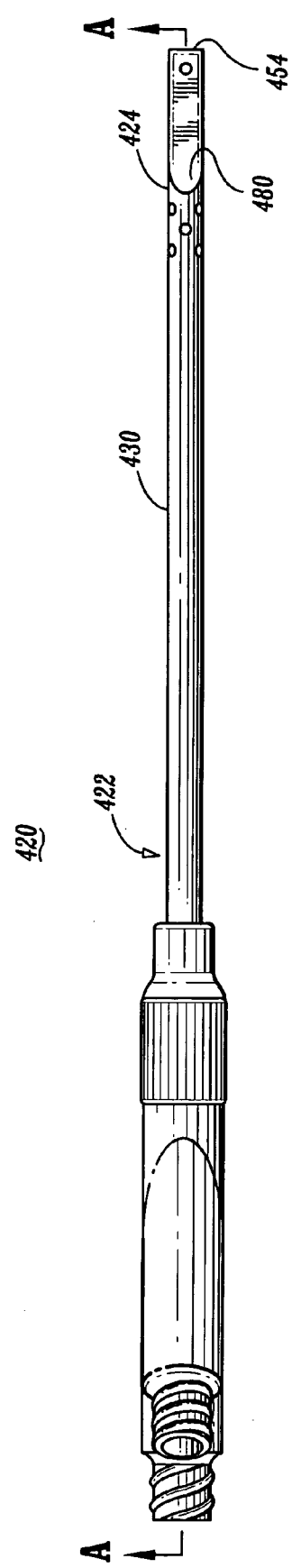
FIG. 16 is a top view of the catheter apparatus shown in FIG. 14.
Figure 17:
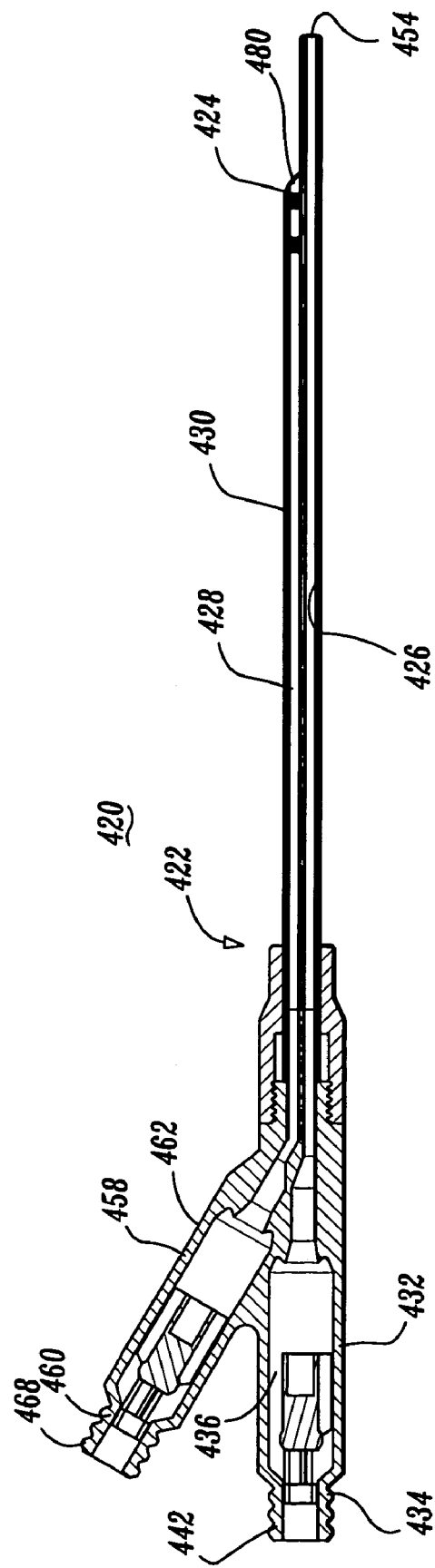
FIG. 17 is a side cross-sectional view, taken along line A—A of FIG. 16, of the catheter apparatus.
Figure 18:
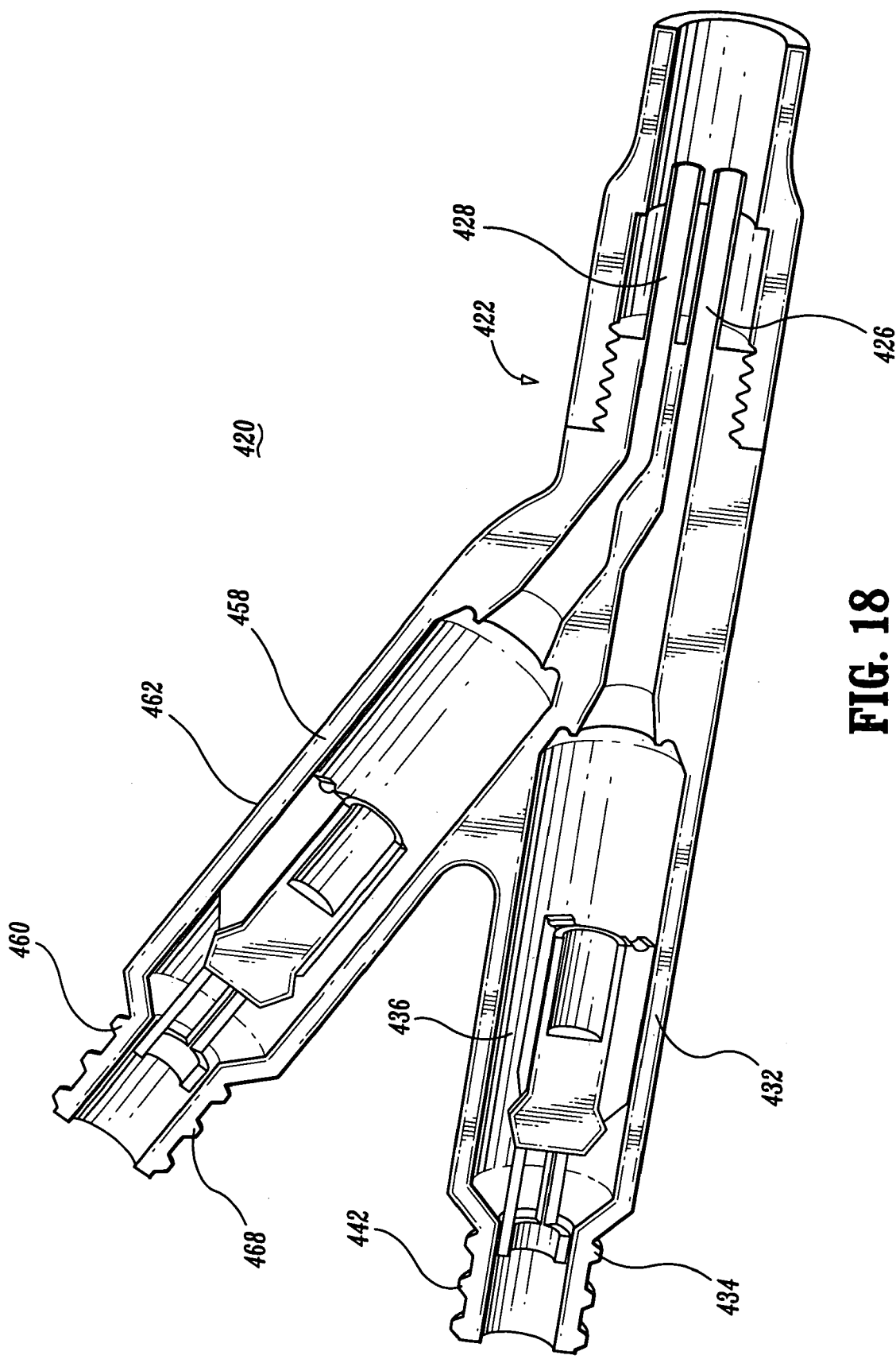
FIG. 18 is an enlarged perspective half section view of the portion of the catheter apparatus shown in FIG. 14.

Referring to FIGS. 12 and 13, in use, a catheter apparatus 220, similar to that described, is assembled, properly sterilized and otherwise prepared for storage, shipment and use in a hemodialysis procedure. A practitioner (not shown) manipulates distal end 224 of tubular body 222 for connection to a body cavity of a subject (not shown). Distal end 224 is inserted within a blood vessel of the subject. Catheter apparatus 220 is employed for administration of fluids that includes the simultaneous introduction of venous blood flow and withdrawal of arterial blood flow. Catheter apparatus 220 is inserted with the blood vessel of the subject such that blood is withdrawn, via arterial blood flow in a first direction, from the blood vessel for treatment by an artificial kidney device (not shown) and the treated blood is introduced back into the blood vessel, via venous blood flow in a second opposite direction.

Initially, the valve configuration that includes first port 254 and second port 280 is in the closed position. Surface 246 of first valve 238 engages surface 248 of proximal end 234 to create a fluid tight seal between first valve 238 and proximal end 234, as discussed. First pusher 244 protrudes from proximal end 234. Surface 272 of second valve 264 engages surface 274 of proximal end 260 to create a fluid tight seal between second valve 264 and proximal end 260. Second pusher 270 protrudes from proximal end 260.

Venous blood line 250 is attached to first luer fitting 242 such that pusher component 252 engages first pusher 244, causing movement of first pusher 244 in a substantially distal direction, as shown by arrow DD, overcoming the bias of spring 250. Surface 246 of first valve 238 disengages from surface 248 of proximal end 234 and the fluid tight seal is interrupted, thereby opening proximal end 234 to establish fluid communication between proximal end 234 and venous lumen 226 as facilitated by openings 289. Venous blood flow is introduced to catheter apparatus 220 through proximal end 234 and into the blood vessel of the subject via venous lumen 226.

Arterial blood line 276 is attached to second luer fitting 268 such that pusher component 278 engages second pusher 270, causing movement of second pusher 270 in a substantially distal direction, as shown by arrow FF, overcoming the bias of spring 266. Surface 272 of second valve 264 disengages from surface 274 of proximal end 260 and the fluid tight seal is interrupted, thereby opening proximal end 260 to establish fluid communication between proximal end 260 and arterial lumen 228. Arterial blood flow may be received by arterial blood line 276.

As first valve 238 is forced distally in the direction shown by arrow DD, discussed above, push rod portion 288 is similarly forced in the direction shown by arrow DD. First port 254 is movable corresponding to the movement of first valve 238, as facilitated by push rod portion 288. The valve configuration that includes first port 254 and second port 280 moves to the open position. First port 254 disengages from second port 280 to interrupt and open the fluid tight seal of second port 280, thereby facilitating fluid communication between second port 280 and arterial lumen 228. Thus, arterial blood flow is withdrawn from the blood vessel and received by arterial lumen 228 for receipt by arterial blood line 276.

In the event that the practitioner desires to discontinue administration of fluids with the subject, the valve configuration that includes first port 254 and second port 280 may be returned to the closed position. Venous blood line 250 is removed from proximal end 234 to recreate the fluid tight seal between first valve 238 and proximal end 234. Push rod portion 288 is caused to move back in the proximal direction, as shown by arrow CC, thereby sealing second port 280. Arterial blood line 276 is removed from proximal end 260 to recreate the fluid tight seal between second valve 264 and proximal end 260.

Referring to FIGS. 14–18, another alternate embodiment of the present disclosure is shown that includes a catheter apparatus 420, similar to those described. Catheter apparatus 420 includes a tubular body 422 having a distal end 424. Distal end 424 includes a cap 425 that is mounted with tubular body 422. Cap 425 is separately formed and configured for assembly with tubular body 422 via threaded engagement. It is contemplated that cap 425 may be assembled by various attachment such as, for example, adhesive, interference or friction, snap engagement, etc.

Tubular body 422 defines a venous lumen 426 and an arterial lumen 428. Venous lumen 426 and arterial lumen 428 are in a substantially side by side orientation along a distal portion 430 of tubular body 422. The distal end of venous lumen 426 extends a greater length relative to the distal end of arterial lumen 428 for connection to the body cavity of a subject. As such, the distal end of arterial lumen 428 is recessed from the distal end of venous lumen 426. Distal portion 430 may include a valve configuration, similar to those described herein with regard to FIGS. 1–13.

Venous lumen 426 includes a tubular venous adapter 432 that extends to a proximal end 434 thereof. Venous adapter 432 defines a valve housing 436, including valve components, and a luer fitting 442, similar to those described herein with regard to FIGS. 1–13. The valve components of valve housing 436 are biased to create a fluid tight seal with proximal end 434.

First luer fitting 442 is configured for attachment to a venous blood line (not shown). The venous blood line is attached to first luer fitting 442 to overcome the bias of the valve components of valve housing 436. The fluid tight seal is interrupted, thereby opening proximal end 434 to establish fluid communication between proximal end 434 and venous lumen 426. Conversely, as the venous blood line is removed from proximal end 434, the bias of the valve components of valve housing 436 recreates the fluid tight seal with proximal end 434. Venous lumen 426 defines a first port 454 disposed adjacent distal end 424 that is configured for fluid flow.

Arterial lumen 428 includes a tubular arterial adapter 458 that extends to a proximal end 460 thereof. Arterial adapter 458 defines a valve housing 462, including valve components, and a second luer fitting 468, similar to those described herein with regard to FIGS. 1–13. The valve components of valve housing 462 are biased to create a fluid tight seal with proximal end 460.

Second luer fitting 468 is configured for attachment to an arterial blood line (not shown). The arterial blood line is attached to second luer fitting 468 to overcome the bias of the valve components of valve housing 462. The fluid tight seal is interrupted, thereby opening proximal end 460 to establish fluid communication between proximal end 460 and arterial lumen 428. Conversely, as the arterial blood line is removed from proximal end 460, the bias of the valve components of valve housing 462 recreates the fluid tight seal with proximal end 460. Arterial lumen 428 defines a second port 480 disposed adjacent distal end 424 that is configured for fluid flow.

In use, catheter apparatus 420, is inserted with the blood vessel of the subject. Tubular body 422 is then reverse tunneled under the skin of a subject (not shown) away from an insertion site to another exit site of the body of the subject. Tubular body 422 is sized as desired and cap 425 is threaded for assembly with tubular body 422. Blood is withdrawn employing arterial lumen 428, via arterial blood flow in a first direction, from the blood vessel for treatment by an artificial kidney device (not shown) and the treated blood is introduced back into the blood vessel employing venous lumen 426, via venous blood flow in a second opposite direction. Catheter apparatus 420 is employed for administration of fluids that includes the simultaneous introduction of venous blood flow and withdrawal of arterial blood flow.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A catheter apparatus, which comprises:
   a tubular body defining a longitudinal axis and having proximal and distal ends, the tubular body defining first and second longitudinal lumens terminating in respective first and second ports adjacent the distal end of the tubular body;
   first and second adapters adjacent the proximal end of the tubular body in fluid communication with the first and second lumens respectively of the tubular body, at least the first adapter including a valve housing and a first valve supported within the valve housing, the first valve adapted for longitudinal movement within the valve housing and relative to the longitudinal axis between a closed position where the first valve substantially seals an interior of the first adapter to prevent flow of fluid and an open position to substantially open the interior of the first adapter to permit flow of fluid; and
   a pusher member connected to the first valve and extending within the tubular body, the pusher member having a distal tip dimensioned to substantially seal at least one of the first and second ports of the tubular body when in a closed position of the distal tip, the pusher member being movable upon movement of the first valve to an open position of the distal tip to thereby open the at least one of the first and second ports to permit flow of fluid therethrough.

2. The catheter apparatus according to claim 1 wherein the first valve is normally longitudinally biased toward the closed position.

3. The catheter apparatus according to claim 2 wherein the distal tip of the pusher member is adapted to substantially seal the second port of the tubular body when in the closed position of the distal tip and is adapted to open the second port when in the open position of the distal tip.

4. The catheter apparatus according to claim 3 wherein the first and second ports define axial openings.

5. The catheter apparatus according to claim 1 wherein the first adapter includes a spring member mounted within the valve housing and engageable with the first valve, the spring member adapted to bias the first valve toward the closed position.

6. The catheter apparatus according to claim 1 wherein the pusher member is adapted for longitudinal movement with the first valve to move the distal tip to the open position thereof.

7. The catheter apparatus according to claim 6 wherein the distal tip of the pusher member is adapted to substantially seal each of the first and second ports of the tubular body when in the closed position of the distal tip.

8. The catheter apparatus according to claim 7 wherein the distal tip is adapted to open each of the first and second ports when in the open position of the distal tip.

9. The catheter apparatus according to claim 8 wherein the first and second ports are lateral ports defined in an outer wall of the tubular body.

10. The catheter apparatus according to claim 1 wherein the second adapter includes a valve housing and a second valve supported within the valve housing, the second valve adapted for longitudinal movement within the valve housing and relative to the longitudinal axis between a closed position where the second valve substantially seals an interior of the second adapter to prevent flow of fluid and an open position to substantially open the interior of the second adapter to permit flow of fluid.

11. The catheter apparatus according to claim 10 wherein the second valve is normally longitudinally biased toward the closed position.

12. The catheter apparatus according to claim 10 wherein the second adapter includes a spring member mounted within the valve housing and engageable with the second valve, the spring member adapted to bias the second valve toward the closed position.

13. The catheter apparatus according to claim 1 wherein the first lumen is a venous lumen adapted to return blood to a patient and wherein the second lumen is an arterial lumen adapted to remove blood from the patient.

14. The catheter apparatus according to claim 1 wherein the distal tip of the pusher member is adapted to establish fluid communication between the first and second lumens upon movement to the open position thereof.

\* \* \* \* \*